United States Patent
Melcher et al.

(10) Patent No.: US 10,453,111 B2
(45) Date of Patent: *Oct. 22, 2019

(54) DATA MESH VISUALIZATION

(71) Applicant: eBay Inc., San Jose, CA (US)

(72) Inventors: Ryan Melcher, Ben Lomond, CA (US); John Tapley, San Jose, CA (US); Robert Lee, Burlingame, CA (US)

(73) Assignee: eBay Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,351

(22) Filed: Dec. 20, 2017

(65) Prior Publication Data

US 2018/0189858 A1 Jul. 5, 2018

Related U.S. Application Data

(63) Continuation of application No. 14/449,113, filed on Jul. 31, 2014, now Pat. No. 9,886,710.

(Continued)

(51) Int. Cl.
*G06Q 30/06* (2012.01)
*H04L 29/08* (2006.01)
*G06T 11/20* (2006.01)
*H04L 12/26* (2006.01)
*H04L 29/12* (2006.01)
(Continued)

(52) U.S. Cl.
CPC ........... *G06Q 30/0631* (2013.01); *A61B 5/04* (2013.01); *G06Q 30/0633* (2013.01); *G06T 11/206* (2013.01); *H04L 43/04* (2013.01); *H04L 61/609* (2013.01); *H04L 63/08* (2013.01); *H04L 63/107* (2013.01); *H04L 67/10* (2013.01); *H04L 67/1042* (2013.01); *H04W 4/80* (2018.02); *H04W 76/14* (2018.02); *H04W 84/18* (2013.01)

(58) Field of Classification Search
CPC .................................. G06Q 30/0633
USPC ......................................................... 345/440
See application file for complete search history.

(56) References Cited

U.S. PATENT DOCUMENTS 5,794,178 A   8/1998   Caid et al.
6,014,661 A   1/2000   Ahlberg et al.
(Continued)

FOREIGN PATENT DOCUMENTS

CN   106462825 A   2/2017
JP   2006-525570 A   11/2006
(Continued)

OTHER PUBLICATIONS

U.S. Appl. No. 14/498,326 U.S. Pat. No. 9,576,312, filed Sep. 26, 2014 Data Mesh-Based Wearable Device Ancillary Activity.

(Continued)

*Primary Examiner* — Javid A Amini
(74) *Attorney, Agent, or Firm* — Schwegman Lundberg & Woessner, P.A.

(57) ABSTRACT

In various example embodiments, a system and method for data mesh visualization are presented. Attribute data associated with a user may be received from a plurality of attribute sources. User characteristics may be inferred based on an analysis of at least a portion of the attribute data. A visualization may be generated based, at least in part, on the user characteristics. The visualization may be representative of the attribute data. The visualization may be caused to be presented to the user.

20 Claims, 19 Drawing Sheets

Related U.S. Application Data

(60) Provisional application No. 61/970,263, filed on Mar. 25, 2014.

(51) Int. Cl.
| | |
|---|---|
| *H04L 29/06* | (2006.01) |
| *H04W 76/14* | (2018.01) |
| *H04W 4/80* | (2018.01) |
| *A61B 5/04* | (2006.01) |
| *H04W 84/18* | (2009.01) |

(56) References Cited

U.S. PATENT DOCUMENTS

| | | | |
|---|---|---|---|
| 6,097,386 | A | 8/2000 | Bardon et al. |
| 6,137,499 | A | 10/2000 | Tesler |
| 6,301,579 | B1 | 10/2001 | Becker |
| 7,483,964 | B1 | 1/2009 | Jackson et al. |
| 7,676,034 | B1 | 3/2010 | Wu et al. |
| 8,095,432 | B1 | 1/2012 | Berman et al. |
| 8,177,260 | B2 | 5/2012 | Tropper et al. |
| 8,463,939 | B1 | 6/2013 | Galvin |
| 8,686,924 | B2 | 4/2014 | Braun et al. |
| 8,908,926 | B2 | 12/2014 | Henderson et al. |
| 9,576,312 | B2 | 2/2017 | Melcher et al. |
| 9,886,710 | B2 | 2/2018 | Melcher et al. |
| 10,304,114 | B2 | 5/2019 | Melcher et al. |
| 2002/0149614 | A1 | 10/2002 | Biebesheimer et al. |
| 2002/0161664 | A1 | 10/2002 | Shaya et al. |
| 2003/0073412 | A1 | 4/2003 | Meade |
| 2003/0229895 | A1 | 12/2003 | Jasinschi et al. |
| 2005/0131716 | A1 | 6/2005 | Hanan et al. |
| 2005/0131894 | A1 | 6/2005 | Vuong |
| 2006/0164324 | A1 | 7/2006 | Polivy et al. |
| 2007/0087313 | A1 | 4/2007 | Vest |
| 2007/0143250 | A1 | 6/2007 | Zigon |
| 2007/0143345 | A1 | 6/2007 | Jones et al. |
| 2007/0174331 | A1 | 7/2007 | Wolf et al. |
| 2007/0244844 | A1* | 10/2007 | Brinson ............... G06K 9/0063 706/46 |
| 2007/0299796 | A1 | 12/2007 | Macbeth et al. |
| 2008/0015953 | A1 | 1/2008 | Harper et al. |
| 2008/0092245 | A1* | 4/2008 | Alward ................. G06F 21/316 726/28 |
| 2008/0146334 | A1 | 6/2008 | Kil |
| 2008/0146343 | A1 | 6/2008 | Sullivan et al. |
| 2008/0183645 | A1 | 7/2008 | Burger et al. |
| 2008/0207220 | A1 | 8/2008 | Aaron |
| 2008/0222706 | A1 | 9/2008 | Renaud et al. |
| 2008/0250408 | A1 | 10/2008 | Tsui et al. |
| 2009/0006525 | A1 | 1/2009 | Moore |
| 2009/0150203 | A1 | 6/2009 | Baudisch et al. |
| 2009/0254971 | A1 | 10/2009 | Herz et al. |
| 2009/0309891 | A1* | 12/2009 | Karkanias ........... G06F 19/3418 345/581 |
| 2010/0125632 | A1* | 5/2010 | Leonard ................ G06Q 10/10 709/204 |
| 2010/0128988 | A1 | 5/2010 | Kincaid |
| 2010/0153868 | A1 | 6/2010 | Allen et al. |
| 2010/0182935 | A1 | 7/2010 | David |
| 2010/0218101 | A1 | 8/2010 | O'Shaughnessy et al. |
| 2010/0231418 | A1 | 9/2010 | Whitlow et al. |
| 2010/0315549 | A1 | 12/2010 | Basso et al. |
| 2011/0015497 | A1 | 1/2011 | Eggenberger et al. |
| 2011/0046805 | A1 | 2/2011 | Bedros et al. |
| 2011/0093780 | A1* | 4/2011 | Dunn ................. G06Q 30/0269 715/706 |
| 2011/0148916 | A1* | 6/2011 | Blattner ............... G06Q 10/107 345/619 |
| 2011/0153663 | A1 | 6/2011 | Koren et al. |
| 2011/0238482 | A1 | 9/2011 | Carney et al. |
| 2011/0295974 | A1 | 12/2011 | Kashef et al. |
| 2012/0014290 | A1 | 1/2012 | David |
| 2012/0059787 | A1* | 3/2012 | Brown ................. G06F 17/241 706/52 |
| 2012/0096076 | A1 | 4/2012 | Chan |
| 2012/0290978 | A1* | 11/2012 | Devecka ................ H04W 4/21 715/810 |
| 2013/0006899 | A1 | 1/2013 | Cook |
| 2013/0119255 | A1 | 5/2013 | Dickinson et al. |
| 2013/0122936 | A1 | 5/2013 | Hudson et al. |
| 2013/0173390 | A1 | 7/2013 | Polo |
| 2013/0214935 | A1 | 8/2013 | Kim et al. |
| 2013/0238538 | A1 | 9/2013 | Cook et al. |
| 2013/0257877 | A1* | 10/2013 | Davis ..................... A63F 13/12 345/473 |
| 2013/0258118 | A1* | 10/2013 | Felt ..................... A45D 44/005 348/207.1 |
| 2013/0262588 | A1* | 10/2013 | Barak ..................... H04L 67/22 709/204 |
| 2013/0275994 | A1 | 10/2013 | Uola et al. |
| 2013/0297688 | A1 | 11/2013 | Zheng |
| 2013/0305185 | A1* | 11/2013 | Nicol, II ............... G06F 3/0481 715/781 |
| 2013/0321446 | A1* | 12/2013 | Cutcher-Gershenfeld ............ G06T 11/206 345/589 |
| 2014/0032723 | A1* | 1/2014 | Nema ................. G06Q 10/00 709/220 |
| 2014/0135644 | A1 | 5/2014 | Kim |
| 2014/0136365 | A1 | 5/2014 | Nista |
| 2014/0173078 | A1 | 6/2014 | McCord et al. |
| 2014/0176335 | A1 | 6/2014 | Brumback et al. |
| 2014/0189829 | A1 | 7/2014 | McLachlan et al. |
| 2014/0279294 | A1* | 9/2014 | Field-Darragh ..... G06Q 10/087 705/28 |
| 2014/0297395 | A1 | 10/2014 | Chao et al. |
| 2015/0018988 | A1 | 1/2015 | Safar |
| 2015/0032541 | A1 | 1/2015 | Haddad et al. |
| 2015/0088598 | A1 | 3/2015 | Acharyya et al. |
| 2015/0120555 | A1* | 4/2015 | Jung ..................... G06Q 20/40 705/44 |
| 2015/0127565 | A1* | 5/2015 | Chevalier ............ G06Q 10/00 705/319 |
| 2015/0253445 | A1 | 9/2015 | Luo et al. |
| 2015/0262282 | A1* | 9/2015 | Walti ................. G06Q 30/0631 705/26.7 |
| 2015/0262458 | A1 | 9/2015 | Faaborg et al. |
| 2015/0269151 | A1 | 9/2015 | Wallace |
| 2015/0278912 | A1* | 10/2015 | Melcher ................ G06T 11/206 705/26.7 |
| 2015/0279069 | A1* | 10/2015 | Melcher ................ G06T 11/206 345/440 |
| 2015/0281009 | A1 | 10/2015 | Melcher et al. |
| 2015/0281252 | A1 | 10/2015 | Melcher et al. |
| 2016/0012129 | A1* | 1/2016 | Rampson ............. G06F 16/951 707/722 |
| 2016/0048595 | A1 | 2/2016 | VanBlon et al. |
| 2016/0048993 | A1* | 2/2016 | Shimomura ........... G06F 3/017 345/629 |
| 2016/0049008 | A1 | 2/2016 | Haddick et al. |
| 2016/0270717 | A1* | 9/2016 | Luna ................. G06F 19/3481 |
| 2017/0171901 | A1 | 6/2017 | Melcher et al. |

FOREIGN PATENT DOCUMENTS

| | | |
|---|---|---|
| KR | 10-2009-0086805 A | 8/2009 |
| KR | 10-2012-0019530 A | 3/2012 |
| KR | 10-2013-0023365 A | 3/2013 |
| WO | 2009108439 | 9/2009 |
| WO | 2015/148559 A1 | 10/2015 |

OTHER PUBLICATIONS

U.S. Appl. No. 15/431,799, filed Feb. 14, 2017 Complementary Activity Based On Availability Of Functionality.
U.S. Appl. No. 14/449,126, filed Jul. 31, 2014 Data Mesh Based Environmental Augmentation.
U.S. Appl. No. 14/449,113 U.S. Pat. No. 9,886,710, filed Jul. 31, 2014 Data Mesh Visualization.

(56) References Cited

OTHER PUBLICATIONS

"U.S. Appl. No. 14/449,126, Response filed Oct. 11, 2018 to Final Office Action dated Jul. 11, 2018", 13 pgs.
"U.S. Appl. No. 15/431,799, Non Final Office Action dated Nov. 1, 2018", 18 pgs.
"U.S. Appl. No. 15/431,799, Response filed Dec. 19, 2018 to Non Final Office Action dated Nov. 1, 2018", 9 pgs.
"Korean Application Serial No. 10-2018-7012784, Response Filed Dec. 21, 2018 to Notice of Preliminary Rejection dated Oct. 2, 2018", (w English Translation), 26 pages.
U.S. Appl. No. 14/449,126, Notice of Allowance dated Jan. 9, 2019, 16 pages.
Corrected Notice of Allowance received for U.S. Appl. No. 14/498,326, dated Dec. 16, 2016, 2 pages.
Examiner Interview Summary received for U.S. Appl. No. 14/449,113, dated Jun. 13, 2017, 4 pages.
Non-Final Office Action received for U.S. Appl. No. 14/449,113, dated Feb. 26, 2016, 15 pages.
Non-Final Office Action received for U.S. Appl. No. 14/449,113, dated Mar. 3, 2017, 15 pages.
Notice of Allowance received for U.S. Appl. No. 14/449,113, dated Sep. 18, 2017, 7 pages.
Response to Non-Final Office Action filed on May 26, 2016 for U.S. Appl. No. 14/449,113, dated Feb. 26, 2016, 12 pages.
Response to Non-Final Office Action filed on Jul. 3, 2017 for U.S. Appl. No. 14/449,113, dated Mar. 3, 2017, 12 pages.
Response to Final Office Action filed on Dec. 5, 2016 for U.S. Appl. No. 14/449,113, dated Aug. 4, 2016, 15 pages.
Examiner Interview Summary received for U.S. Appl. No. 14/449,126, dated Mar. 21, 2017, 3 pages.
Examiner Interview Summary received for U.S. Appl. No. 14/449,126, dated Aug. 11, 2017, 2 pages.
Examiner Interview Summary received for U.S. Appl. No. 14/449,126, dated Sep. 22, 2016, 5 pages.
Final Office Action received for U.S. Appl. No. 14/449,126, dated Jun. 2, 2017, 22 pages.
Final Office Action received for U.S. Appl. No. 14/449,126, dated Jun. 17, 2016, 20 pages.
Non-Final Office Action received for U.S. Appl. No. 14/449,126, dated Oct. 23, 2015, 20 pages.
Non-Final Office Action received for U.S. Appl. No. 14/449,126, dated Nov. 16, 2017, 21 pages.
Non-Final Office Action received for U.S. Appl. No. 14/449,126, dated Nov. 21 2016, 20 pages.
Response to Non-Final Office Action filed on Mar. 21, 2017 for U.S. Appl. No. 14/449,126, dated Nov. 21 2016, 15 pages.
Response to Non-Final Office Action filed on Mar. 23, 2016 for U.S. Appl. No. 14/449,126, dated Oct. 23, 2015, 14 pages.
Response to Final Office Action filed on Oct. 2, 2017 for U.S. Appl. No. 14/449,126, dated Jun. 2, 2017, 17 pages.
Response to Final Office Action filed on Oct. 17, 2016 for U.S. Appl. No. 14/449,126, dated Jun. 17, 2016, 14 pages.
Yu et al., "Application Mobility in Pervasive Computing: A Survey", Pervasive and Mobile Computing, Feb. 2013, pp. 2-17.
Park et al., "Design Patterns for Context-Aware Services", Multimed Tools, Apr. 23, 2014, pp. 2337-2358.
Selan et al, "Using a Rendering Engine to Support the Development of Immersive Virtual Reality Applications", Human-Computer Interfaces, and Measurement Systems, Jul. 2008, pp. 14-16.
Corrected Notice of Allowance received for U.S. Appl. No. 14/498,326, dated Nov. 8, 2016, 2 pages.
Final Office Action received for U.S. Appl. No. 14/449,113, dated Aug. 4, 2016, 21 pages.
First Action Interview—Office Action Summary received for U.S. Appl. No. 14/498,326, dated Jun. 13, 2016, 5 pages.
First Action Interview Pre-Interview Communication received for U.S. Appl. No. 14/498,326, dated Feb. 2, 2016, 4 pages.
Notice of Allowance received for U.S. Appl. No. 14/498,326, dated Oct. 7, 2016, 16 pages.
Response to First Action Interview Pre-Interview Communication filed on Apr. 4, 2016 for U.S. Appl. No. 14/498,326, dated Feb. 2, 2016, 8 pages.
Response to First Action Interview—Office Action Summary filed on Aug. 15, 2016 for U.S. Appl. No. 14/498,326, dated Jun. 13, 2016, 15 pages.
Non Final Office Action received for U.S. Appl. No. 15/431,799, dated Dec. 29, 2017, 15 pages.
Preliminary Amendment for U.S. Appl. No. 15/431,799, filed on Mar. 2, 2017, 9 pages.
International Preliminary Report on Patentability received for PCT Patent Application No. PCT/US2015/022318, dated Oct. 6, 2016, 9 pages.
International Search Report received for PCT Patent Application No. PCT/US2015/022318, dated Jul. 1, 2015, 2 pages.
International Written Opinion received for PCT Patent Application No. PCT/US2015/022318, dated Jul. 1, 2015, 11 pages.
Final Office Action received for Korean Patent Application No. 10-2016-7029553, dated Nov. 30, 2017, 4 pages English Translation.
Office Action received for Korean Patent Application No. 10-2016-7029553, dated Mar. 5, 2018, 17 pages (Official Copy Only).
Office Action received for Korean Patent Application No. 10-2016-7029553, dated May 18, 2017, 13 pages.
Response to Final Office Action filed on Jan. 30, 2018 for Korean Patent Application No. 10-2016-7029553, dated Nov. 30, 2017, 34 pages.
Response to Office Action filed on Jul. 18, 2017 for Korean Patent Application No. 10-2016-7029553, dated May 18, 2017, 29 pages (24 pages of Offical Copy and 5 pages of English Translation).
Bachvarov et al., "Immersive Representation of Objects in Virtual Reality Environment Implementing Impicit Properties", Developments in E-systems Engineering (DeSE), Dec. 2011, pp. 587-592.
Akay et al., "Perceptualization of Biomedical Data", Information Technologies in Medicine, vol. 1: Medical Simulation and Education, Chapter 7, 2001, pp. 189-204.
U.S. Appl. No. 15/431,799, Response filed Apr. 4, 2018 to Non Final Office Action dated Dec. 29, 2017, 12 pages.
Office Action received for Chinese Patent Application No. 201580027971.8, dated Jan. 30, 2019, 58 pages (22 pages of English Translation and 36 pages of Official Copy).
Final Office Action received for U.S. Appl. No. 15/431,799, dated Apr. 2, 2019, 17 pages.
Office Action received for Korean Patent Application No. 10-2018-7012784, dated Mar. 29, 2019, 10 pages (2 pages of English Translation and 8 pages of Official Copy).
"U.S. Appl. No. 14/449,126, Final Office Action dated Jul. 11, 2018", 30 pgs.
"U.S. Appl. No. 15/431,799, Final Office Action dated Jul. 12, 2018", 17 pgs.
"U.S. Appl. No. 15/431,799, Response filed Sep. 12, 2018 to Final Office Actio dated Jul. 12, 2018", 9 pgs.
"U.S. Appl. No. 15/431,799, Advisory Action dated Sep. 20, 2018", 3 pages.
"Response to Non-Final Office Action filed on Apr. 3, 2018, for U.S. Appl. No. 14/449,126, dated Nov. 16, 2017", (Apr. 3, 2018), 17 pages.
"Korean Application Serial No. 10-2018-7012784, Notice of Preliminary Rejection dated Oct. 2, 2018", w English translation, 7 pgs.
"Examiner-Initiated Interview Summary received for U.S. Appl. No. 15/431,799, dated Sep. 20, 2018", (Sep. 20, 2018), 1 page.
Chen, "Real-time smartphone sensing and recommendations towards context-awareness shopping", Springer-Verlag Berlin Heidelberg 2013, (Dec. 6, 2013), 61-72.
Park, "Location-Based Recommendation System Using Bayesian User's Preference Modelin Mobile Devices", Springer-Verlag Berlin Heidelberg 2007UIC 2007, LNCS 4611, (2007), 1130-1139.
Yeh, "Intelligent service-integrated platform based on the RFID technology and software agent system", journal homepage: www.elsevier.com locale eswa, Elsevier L TO, vol. 38, Issue 4, (Apr. 2011), 3058-3068.

(56) References Cited

OTHER PUBLICATIONS

Response to Office Action filed on May 29, 2019, for Korean Patent Application No. 10-2018-7012784, dated Mar. 29, 2019, 13 pages(3 pages of English Translation and 10 pages of Official Copy).
Response to Final Office Action filed on May 20, 2019 for U.S. Appl. No. 15/431,799, dated Apr. 2, 2019, 10 pages.
Response to Office Action filed on Jun. 4, 2019, for Chinese Patent Application No. 201580027971.8, dated Jan. 30, 2019, 14 pages(3 pages of English Translation and 11 pages of Official Copy).
Non-Final Office Action received for U.S. Appl. No. 15/431,799, dated Jun. 13, 2019, 27 pages.
Applicant Interview summary received for U.S. Appl. No. 15/431,799 dated Aug. 7, 2019, 3 pages.
Response to Non-Final Office Action Filed on Aug. 21, 2019, for U.S. Appl. No. 15/431,799 dated Jun. 13, 2019, 12 pages.
Office Action received for Korean patent Application No. 10-2018-7012784, dated Jul. 15, 2019, 13 pages (6 pages of English Translation and 7 pages of Official copy).
Office Action received for Chinese patent Application No. 201580027971.8, dated Jul. 17, 2019, 37 pages (14 pages of Official copy and 23 pages of English Translation).
U.S. Appl. No. 16/391,852, Preliminary Amendment filed Sep. 9, 2019, 7 pages.

\* cited by examiner

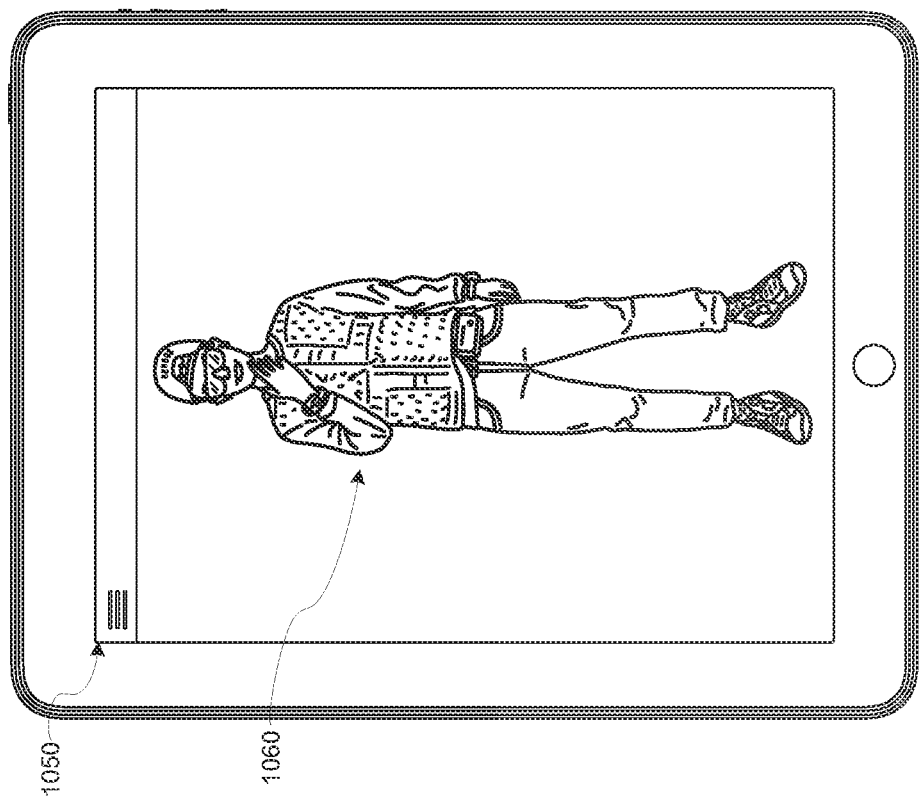
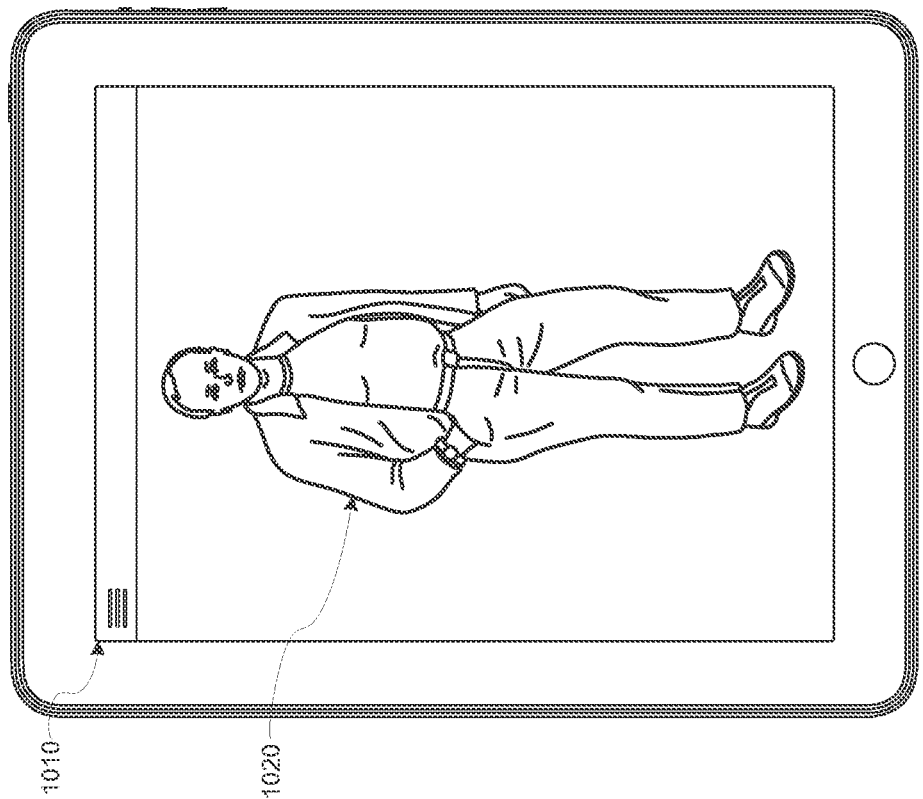
FIG. 10B
FIG. 10A

1500

DEVICE 1422
- DEVICE ID
- DEVICE NAME
- RESOURCES
- I/O COMPONENT DATA

POSITION DATA 1504
- LOCATION DATA
- ORIENTATION DATA
- BEACON DETECTIONS

LOCATION DATA 1506
- LATITUDE
- LONGITUDE
- ALTITUDE
- TIME STAMP

MOTION DATA 1508
- ACCELERATION IN X, Y, AND Z AXES
- VELOCITY
- ANGULAR ACCELERATION

ENVIRONMENTAL DATA 1510
- AMBIENT TEMPERATURE
- ATMOSPHERIC PRESSURE
- LUMINOSITY
- ACOUSTIC DECIBEL LEVEL

BIOMETRIC DATA 1512
- BLOOD PRESSURE
- HEART RATE
- GLUCOSE LEVEL
- BODY TEMPERATURE

STANDARD DEVICE PARAMETERS 1502
- aliveTime (sec)
- batteryLevel (integer %)
- batteryVoltage (Volts)
- current (Amps)
- currentBillingRate (Money)
- daylLghtSavingsTime (boolean)
- dimmerValue (integer)
- accumluatedEnergy (Wh)
- deviceIdentify (sec; noise/blink. etc.)
- illuminance (lux)
- InternalURLOfDevice (string)
- model (string)
- outletStatus (string; ON/OFF)
- packetErrorRateForServicibility (int)
- power (Watts)
- measuredPowerFactor (pf)
- uploadInterval (sec)
- accumulatedEnergy (VArh)
- numberOfReboots (int)
- timeToReboot (sec)
- receiverSignalStrengthIndicator (dBm)
- signalStrentgh (int; 0-100%)
- temp (degrees Fahrenheit )
- targetTempCool (degrees Fahrenheit )
- targetTempHeat (degrees Fahrenheit )
- measuredVoltage (Volts)
- timeZone (minutes from UTC)

*FIG. 15*

DATA MESH VISUALIZATION

RELATED APPLICATIONS

This applications a continuation of U.S. application Ser. No. 14/449,113, filed Jul. 31, 2014, which claims the priority benefit of U.S. Provisional Application No. 61/970,263, filed Mar. 25, 2014, each of which is hereby incorporated by reference in its entirety.

TECHNICAL FIELD

Embodiments of the present disclosure relate generally to data processing and, more particularly, but not by way of limitation, to data mesh visualization.

BACKGROUND

In recent years mobile devices, wearable devices, smart devices, and the like have pervaded nearly every aspect of modern life. Such devices are increasingly incorporating sensors to monitor everything from the moisture level of houseplants to the dribbling of a basketball. Network connected devices like these are capable of providing a near real-time and constant data feed. These trends have provided a vast amount of rich, constantly updated data.

BRIEF DESCRIPTION OF THE DRAWINGS

Various ones of the appended drawings merely illustrate example embodiments of the present disclosure and cannot be considered as limiting its scope.

FIGS. 8, 9, 10A and 10B depict example user interfaces including example visualizations, according to some example embodiments.

FIG. 15 is a block diagram of an example data structure for example attribute data associated with a device, according to some example embodiments.

Figure 1A:
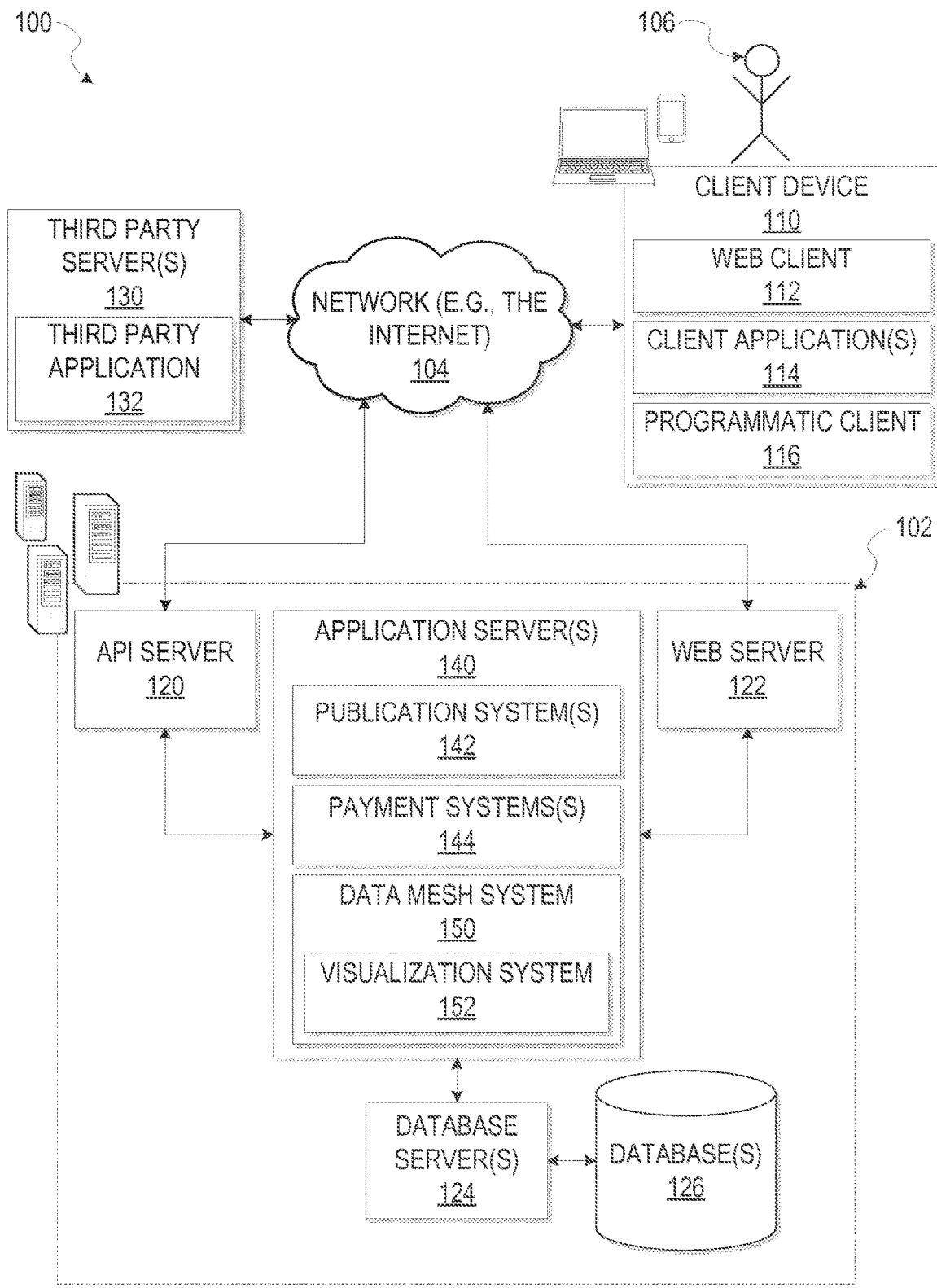
FIG. 1A is a block diagram illustrating a networked system, according to some example embodiments.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

In various example embodiments, a visualization may be generated based, at least in part, on attribute data associated with a user. In an example embodiment, attribute data may be received from a broad gamut of attribute sources. For instance, the attribute data may include data associated with the user received from mobile devices, smart devices, smart homes, social network services, user profiles, browsing histories, or purchase histories. The collective, aggregated attribute data may be referred to as a "data mesh." Subsequent to receiving the attribute data, a user characteristic may be inferred based on an analysis of at least a portion of the attribute data. In various example embodiments, the user characteristic may be a trait, quality, action, activity, attitude, health condition, habit, behavior, and the like. For example, physical characteristics of the user such as height, weight, fitness level, and so on, may be inferred or measured directly from the attribute data. In an example embodiment, a visualization may be generated based, at least in part, on the user characteristic. The visualization may be representative of the attribute data. For example, the visualization may be an avatar that includes physical characteristics similar to the user. In this example, the visualization may be representative of the user. The visualization may be caused to be presented to the user.

In further example embodiments, the user may provide user input indicating a change to the visualization. The visualization may be updated according to the change indicated by the user input. Subsequent inferred user characteristics may be based, at least in part, on the user input. For example, if the visualization does not accurately reflect the user or the attribute data, the user may modify the visualization. The modification may then be used as a basis to more accurately generate the visualization or more accurately infer the user characteristics.

In still further example embodiments, a reward may be provided to the user based on a determined satisfaction of reward criteria. For instance, the reward criteria may include a criterion to complete a physical activity such as a certain number of steps taken as determined by a pedometer (e.g., an application executing on a mobile device of the user that may determine steps taken). Based on exceeding a threshold number of steps taken, the user may satisfy the reward criteria. In an example embodiment, the reward may include additional feature for the visualization (e.g., an additional accessory or function for the visualization). In another instance, the reward criteria may be associated with completeness of a profile. In this instance, the more information the user provides or provides permission to access, the closer the user may be to satisfying the reward criteria.

With reference to FIG. 1A, an example embodiment of a high-level client-server-based network architecture 100 is shown. A networked system 102 provides server-side functionality via a network 104 (e.g., the Internet or wide area network (WAN)) to a client device 110. A user (e.g., user 106) may interact with the networked system 102 using the client device 110. FIG. 1A illustrates, for example, a web client 112 (e.g., a browser, such as the Internet Explorer® browser developed by Microsoft® Corporation of Redmond, Wash. State), client application(s) 114, and a programmatic client 116 executing on the client device 110. The client device 110 may include the web client 112, the client application(s) 114, and the programmatic client 116 alone, together, or in any suitable combination. Although FIG. 1A shows one client device 110, multiple client devices may be included in the network architecture 100.

The client device 110 may comprise a computing device that includes at least a display and communication capabilities that provide access to the networked system 102 via the network 104. The client device 110 may comprise, but is not limited to, a remote device, work station, computer, general purpose computer, Internet appliance, hand-held device, wireless device, portable device, wearable computer, cellular or mobile phone, personal digital assistant (PDA), smart phone, tablet, ultrabook, netbook, laptop, desktop, multi-processor system, microprocessor-based or programmable consumer electronic, game consoles, set-top box, network PC, mini-computer, and the like. In further example embodiments, the client device 110 may comprise one or more of a touch screen, accelerometer, gyroscope, biometric sensor, camera, microphone, global positioning system (GPS) device, and the like.

The client device 110 may communicate with the network 104 via a wired or wireless connection. For example, one or more portions of the network 104 may be an ad hoc network, an intranet, an extranet, a Virtual Private Network (VPN), a Local Area Network (LAN), a wireless LAN (WLAN), a Wide Area Network (WAN), a wireless WAN (WWAN), a Metropolitan Area Network (MAN), a portion of the Internet, a portion of the Public Switched Telephone Network (PSTN), a cellular telephone network, a wireless network, a Wireless Fidelity (Wi-Fi®) network, a Worldwide Interoperability for Microwave Access (WiMax) network, another type of network, or a combination of two or more such networks.

The client device 110 may include one or more of the applications (also referred to as "apps") such as, but not limited to, web browsers, book reader apps (operable to read e-books), media apps (operable to present various media forms including audio and video), fitness apps, biometric monitoring apps, messaging apps, electronic mail (email) apps, e-commerce site apps (also referred to as "marketplace apps"), and so on. The client application(s) 114 may include various components operable to present information to the user and communicate with networked system 102. In some embodiments, if the e-commerce site application is included in the client device 110, then this application may be configured to locally provide the user interface and at least some of the functionalities with the application configured to communicate with the networked system 102, on an as needed basis, for data or processing capabilities not locally available (e.g., access to a database of items available for sale, to authenticate a user, to verify a method of payment). Conversely, if the e-commerce site application is not included in the client device 110, the client device 110 may use its web browser to access the e-commerce site (or a variant thereof) hosted on the networked system 102.

In various example embodiments, the users (e.g., the user 106) may be a person, a machine, or other means of interacting with the client device 110. In some example embodiments, the users may not be part of the network architecture 100, but may interact with the network architecture 100 via the client device 110 or another means. For instance, the users may interact with client device 110 that may be operable to receive input information from (e.g., using touch screen input or alphanumeric input) and present information to (e.g., using graphical presentation on a device display) the users. In this instance, the users may, for example, provide input information to the client device 110 that may be communicated to the networked system 102 via the network 104. The networked system 102 may, in response to the received input information, communicate information to the client device 110 via the network 104 to be presented to the users. In this way, the user may interact with the networked system 102 using the client device 110.

An Application Program Interface (API) server 120 and a web server 122 may be coupled to, and provide programmatic and web interfaces respectively to, one or more application server(s) 140. The application server(s) 140 may host one or more publication system(s) 142, payment system(s) 144, and a data mesh system 150, each of which may comprise one or more modules or applications and each of which may be embodied as hardware, software, firmware, or any combination thereof. The application server(s) 140 are, in turn, shown to be coupled to one or more database server(s) 124 that facilitate access to one or more information storage repositories or database(s) 126. In an example embodiment, the database(s) 126 are storage devices that store information to be posted (e.g., publications or listings) to the publication system(s) 142. The database(s) 126 may also store digital goods information in accordance with some example embodiments.

Additionally, a third party application 132, executing on a third party server 130, is shown as having programmatic access to the networked system 102 via the programmatic interface provided by the API server 120. For example, the third party application 132, utilizing information retrieved from the networked system 102, may support one or more features or functions on a website hosted by the third party. The third party website may, for example, provide one or more promotional, marketplace, or payment functions that are supported by the relevant applications of the networked system 102.

The publication system(s) 142 may provide a number of publication functions and services to the users that access the networked system 102. The payment system(s) 144 may likewise provide a number of functions to perform or facilitate payments and transactions. While the publication system(s) 142 and payment system(s) 144 are shown in FIG. 1A to both form part of the networked system 102, it will be appreciated that, in alternative embodiments, each system 142 and 144 may form part of a payment service that is separate and distinct from the networked system 102. In some example embodiments, the payment system(s) 144 may form part of the publication system(s) 142.

The data mesh system 150 may provide functionality to receive, retrieve, or store a broad spectrum of data associated with the users and other users. It will be noted that the collective, aggregated attribute data may be referred to as a "data mesh." In an example embodiment, the data mesh system 150 may include a visualization system 152 that may generate a visualization representative of data associated with the users and facilitate the presentation of the visualization to the users. In some example embodiments, the data mesh system 150 may communicate with the client device 110, the third party server(s) 130, the publication system(s) 142 (e.g., retrieving listings), and the payment system(s) 144 (e.g., purchasing a listing). In an alternative example embodiment, the data mesh system 150 may be a part of the publication system(s) 142.

Further, while the client-server-based network architecture 100 shown in FIG. 1A employs a client-server architecture, the present inventive subject matter is, of course, not limited to such an architecture, and may equally well find application in a distributed, or peer-to-peer, architecture system, for example. The various systems of the applications server(s) 140 (e.g., the publication system(s) 142 and the payment system(s) 144) may also be implemented as standalone software programs, which do not necessarily have networking capabilities.

The web client 112 may access the various systems of the networked system 102 (e.g., the publication system(s) 142) via the web interface supported by the web server 122. Similarly, the programmatic client 116 and client application(s) 114 may access the various services and functions provided by the networked system 102 via the programmatic interface provided by the API server 120. The programmatic client 116 may, for example, be a seller application (e.g., the Turbo Lister application developed by eBay® Inc., of San Jose, Calif.) to enable sellers to author and manage listings on the networked system 102 in an off-line manner, and to perform batch-mode communications between the programmatic client 116 and the networked system 102.

Figure 1B:
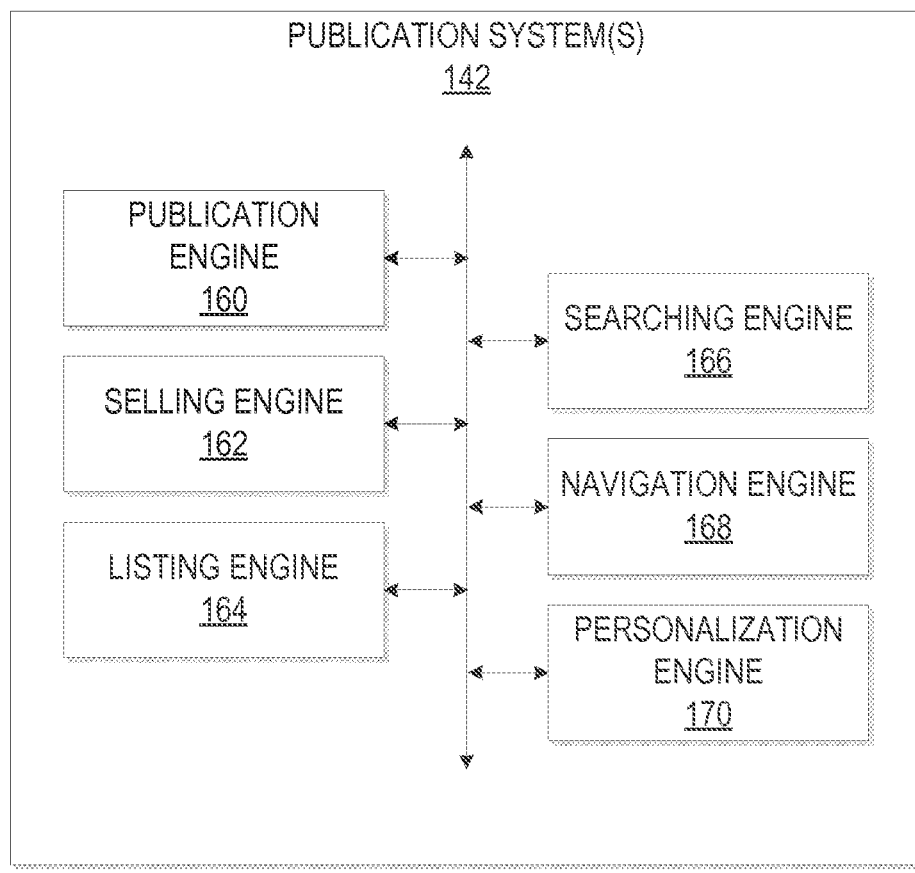
FIG. 1B illustrates a block diagram showing components provided within the system of FIG. 1A, according to some example embodiments.

FIG. 1B illustrates a block diagram showing components provided within the publication system(s) 142, according to some embodiments. In various example embodiments, the publication system(s) 142 may comprise a market place system to provide market place functionality (e.g., facilitating the purchase of items associated with item listings on an e-commerce website). The networked system 102 may be hosted on dedicated or shared server machines that are communicatively coupled to enable communications between server machines. The components themselves are communicatively coupled (e.g., via appropriate interfaces) to each other and to various data sources, so as to allow information to be passed between the applications or so as to allow the applications to share and access common data. Furthermore, the components may access one or more database(s) 126 via the database server(s) 124.

The networked system 102 may provide a number of publishing, listing, and price-setting mechanisms whereby a seller (also referred to as a "first user") may list (or publish information concerning) goods or services for sale or barter, a buyer (also referred to as a "second user") can express interest in or indicate a desire to purchase or barter such goods or services, and a transaction (such as a trade) may be completed pertaining to the goods or services. To this end, the networked system 102 may comprise a publication engine 160 and a selling engine 162. The publication engine 160 may publish information, such as item listings or product description pages, on the networked system 102. In some embodiments, the selling engine 162 may comprise one or more fixed-price engines that support fixed-price listing and price setting mechanisms and one or more auction engines that support auction-format listing and price setting mechanisms (e.g., English, Dutch, Chinese, Double, Reverse auctions, etc.). The various auction engines may also provide a number of features in support of these auction-format listings, such as a reserve price feature whereby a seller may specify a reserve price in connection with a listing and a proxy-bidding feature whereby a bidder may invoke automated proxy bidding. The selling engine 162 may further comprise one or more deal engines that support merchant-generated offers for products and services.

A listing engine 164 allows sellers to conveniently author listings of items or authors to author publications. In one embodiment, the listings pertain to goods or services that a user (e.g., a seller) wishes to transact via the networked system 102. In some embodiments, the listings may be an offer, deal, coupon, or discount for the good or service. Each good or service is associated with a particular category. The listing engine 164 may receive listing data such as title, description, and aspect name/value pairs. Furthermore, each listing for a good or service may be assigned an item identifier. In other embodiments, a user may create a listing that is an advertisement or other form of information publication. The listing information may then be stored to one or more storage devices coupled to the networked system 102 (e.g., database(s) 126). Listings also may comprise product description pages that display a product and information (e.g., product title, specifications, and reviews) associated with the product. In some embodiments, the product description page may include an aggregation of item listings that correspond to the product described on the product description page.

The listing engine 164 also may allow buyers to conveniently author listings or requests for items desired to be purchased. In some embodiments, the listings may pertain to goods or services that a user (e.g., a buyer) wishes to transact via the networked system 102. Each good or service is associated with a particular category. The listing engine 164 may receive as much or as little listing data, such as title, description, and aspect name/value pairs, that the buyer is aware of about the requested item. In some embodiments, the listing engine 164 may parse the buyer's submitted item information and may complete incomplete portions of the listing. For example, if the buyer provides a brief description of a requested item, the listing engine 164 may parse the description, extract key terms and use those terms to make a determination of the identity of the item. Using the determined item identity, the listing engine 164 may retrieve additional item details for inclusion in the buyer item request. In some embodiments, the listing engine 164 may assign an item identifier to each listing for a good or service.

In some embodiments, the listing engine 164 allows sellers to generate offers for discounts on products or services. The listing engine 164 may receive listing data, such as the product or service being offered, a price or discount for the product or service, a time period for which the offer is valid, and so forth. In some embodiments, the listing engine 164 permits sellers to generate offers from a sellers' mobile devices. The generated offers may be uploaded to the networked system 102 for storage and tracking.

Searching the networked system 102 is facilitated by a searching engine 166. For example, the searching engine 166 enables keyword queries of listings published via the networked system 102. In example embodiments, the searching engine 166 receives the keyword queries from a device of a user and conducts a review of the storage device storing the listing information. The review will enable compilation of a result set of listings that may be sorted and returned to the client device 110 of the user. The searching engine 166 may record the query (e.g., keywords) and any subsequent user actions and behaviors (e.g., navigations, selections, or click-throughs).

The searching engine 166 also may perform a search based on a location of the user. A user may access the searching engine 166 via a mobile device and generate a search query. Using the search query and the user's location, the searching engine 166 may return relevant search results for products, services, offers, auctions, and so forth to the user. The searching engine 166 may identify relevant search results both in a list form and graphically on a map. Selection of a graphical indicator on the map may provide additional details regarding the selected search result. In some embodiments, the user may specify, as part of the search query, a radius or distance from the user's current location to limit search results.

In a further example, a navigation engine 168 allows users to navigate through various categories, catalogs, or inventory data structures according to which listings may be classified within the networked system 102. For example, the navigation engine 168 allows a user to successively navigate down a category tree comprising a hierarchy of categories (e.g., the category tree structure) until a particular set of listings is reached. Various other navigation applications within the navigation engine 168 may be provided to supplement the searching and browsing applications. The navigation engine 168 may record the various user actions (e.g., clicks) performed by the user in order to navigate down the category tree.

In some example embodiments, a personalization engine 170 may allow the users of the networked system 102 to personalize various aspects of their interactions with the networked system 102. For instance, the users may define, provide, or otherwise communicate personalization settings that the personalization engine 170 may use to determine interactions with the networked system 102. In further example embodiments, the personalization engine 170 may automatically determine personalization settings and personalize interactions based on the automatically determined settings. For example, the personalization engine 170 may determine a native language of the user and automatically present information in the native language.

Figure 2A:
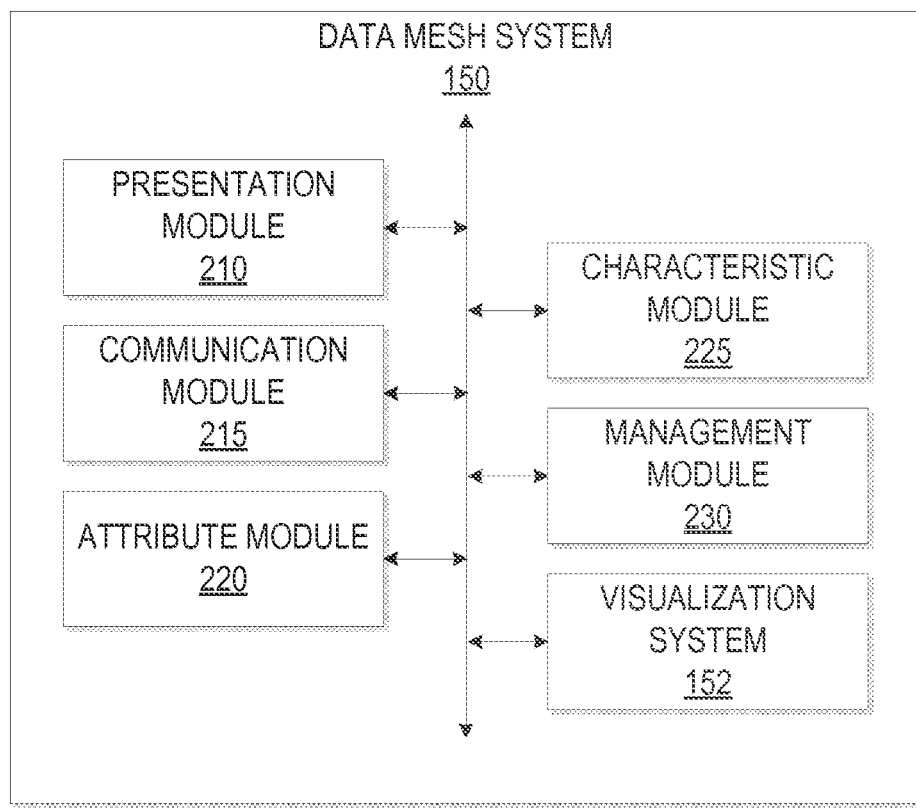
FIG. 2A is a block diagram illustrating an example embodiment of a data mesh system, according to some example embodiments.
Figure 2B:
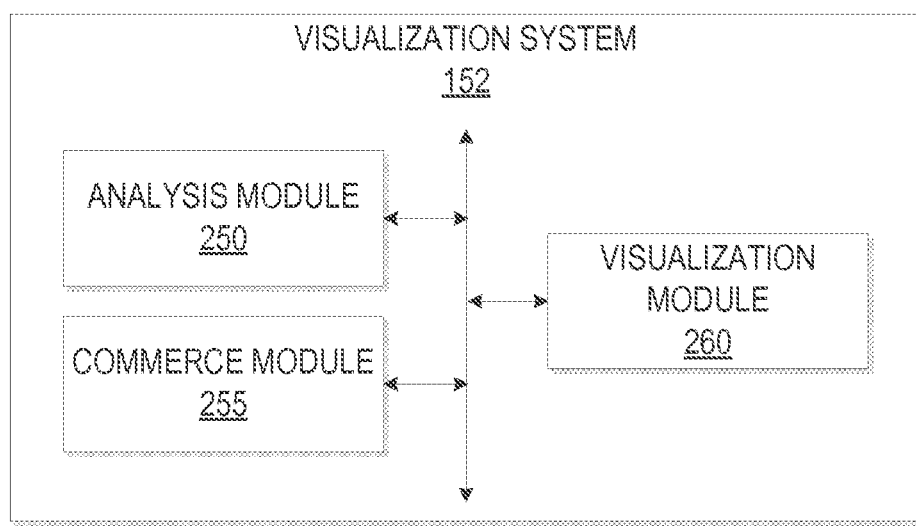
FIG. 2B is a block diagram illustrating an example embodiment of a visualization system, according to some example embodiments.

FIG. 2A is a block diagram of the data mesh system 150, which may provide functionality to receive, retrieve, or access attribute data from attribute sources, analyze the attribute data, manage the attribute data, and so forth. In an example embodiment, the data mesh system 150 may include a presentation module 210, a communication module 215, an attribute module 220, a characteristic module 225, a management module 230, and the visualization system 152. FIG. 2B is a block diagram of the visualization system 152, which may provide functionality to analyze the attribute data and generate a visualization based on the attribute data. The visualization system 152 may include an analysis module 250, a commerce module 255, and a visualization module 260. All, or some, of the modules 210-260 of FIGS. 2A and 2B may communicate with each other, for example, via a network coupling, shared memory, and the like. It will be appreciated that each module of modules 210-260 may be implemented as a single module, combined into other modules, or further subdivided into multiple modules. It will further be appreciated that the modules or functionality of the visualization system 152 may be implemented in the data mesh system 150 and the modules or functionality of the data mesh system 150 may be implemented in the visualization system 152. Other modules not pertinent to example embodiments may also be included, but are not shown.

Referring to FIG. 2A, the presentation module 210 may provide various presentation and user interface functionality operable to interactively present and receive information from users. For example, the presentation module 210 may cause presentation of the visualization based on the attribute data to the user. The presentation module 210 may present or cause presentation of information using a variety of means including visually displaying information and using other device outputs (e.g., acoustic, haptic). Interactively presenting is intended to include the exchange of information between a device and a user. The user may provide input to interact with the user interface in a variety of ways including alphanumeric input, cursor input, tactile input, or other input (e.g., one or more touch screen, camera, tactile sensors, light sensors, infrared sensors, biometric sensors, microphone, gyroscope, accelerometer, or other sensors). It will be appreciated that the presentation module 210 may provide many other user interfaces to facilitate functionality described herein. Further, it will be appreciated that "presenting" as used herein is intended to include communicating information to another device with functionality operable to perform presentation using the communicated information.

The communication module 215 may provide various communications functionality and web services. For example, network communication such as communicating with the networked system 102, the client device 110, and the third party server(s) 130 may be provided. In various example embodiments, the network communication may operate over wired or wireless modalities. Web services are intended to include retrieving information from the third party server(s) 130, the database(s) 126, and the application server(s) 140. Information retrieved by the communication module 215 may comprise data associated with the user (e.g., user profile information from an online account, social network service data associated with the user), data associated with one or more items listed on an e-commerce website (e.g., images of the item, reviews of the item, item price), or other data to facilitate the functionality described herein.

The attribute module 220 may receive, access, or retrieve a wide variety of attribute data from many different attribute sources. For example, the attribute module 220 may receive, retrieve, or access the attribute data from user devices or machines (e.g., the client device(s) 110), social network services, the third party server(s) 130, the publication system(s) 142, the payment system(s) 144, other applications servers, or other attribute sources. The attribute data, as used herein, is intended to include raw data such as sensor data, profile data, social network content, and so on.

In some example embodiments, the attribute module 220 may extract the attribute data from various sources. For instance, a payment history log of the user may include a tremendous amount of extraneous data. The attribute module 220 may extract purchase information such as item purchased, time, purchase price, seller, location, brand, and so forth from the payment history log of the user.

In further example embodiments, the attribute module 220 may perform various functions to prepare or condition the attribute data for analysis. For instance, the attribute module 220 may standardize the attribute data to facilitate analysis of the attribute data (e.g., determine a normal form for the data to allow for comparison and other mathematical analysis). The attribute module 220 may perform many other functions to prepare the attribute data for analysis.

In various example embodiments, the attribute module 220 may store the attribute data in association with the user for subsequent analysis. For example, the attribute module 220 may store the attribute data in the database(s) 126. The attribute data may be stored in conjunction with a user identifier such that the attribute module 220 may subsequently use the user identifier to access the attribute data corresponding to a particular user. The attribute module 220 may access the stored attribute data using other schemes. For instance, the attribute module 220 may access a portion of the attribute data associated with a time, an item, a user, a type of user, a particular attribute source, and so forth. In this way, the attribute module 220 may access a portion of attribute data according to various parameters from among a large quantity of the attribute data to access, identify, or find pertinent or relevant data.

The characteristic module 225 may infer a user characteristic or multiple user characteristics corresponding to the user based on an analysis of at least a portion of the attribute data. Many schemes and techniques may be employed to infer the characteristic from the attribute data. For example, a particular user characteristic may be a work location of the user. The attribute data may include a plurality of locations (e.g., as determined by a GPS component of a user device used by the user) that include time stamps. The work location of the user may be inferred based on the consistency and timing of the locations included in the attribute data (e.g., during normal working hours, the user is typically at a particular office building). Many different portions of attribute data and combinations of portions of attribute data may be analyzed to infer a wide variety of characteristics.

In various example embodiments, characteristics (e.g., the user characteristics), as used herein, are intended to include traits, qualities, actions, activities, attitudes, habits, behaviors, and the like pertaining to a person or people. Inasmuch as the attribute data may not necessarily pertain to a person (e.g., raw data such as coordinates of a particular location), a characteristic (e.g., current location of the user, disliking spicy food, having young children, being a Star Trek fanatic) may be distinct from the attribute data.

The management module 230 may provide management functions associated with the attribute data. For example, the management module 230 may provide the user with functionality to edit, modify, update, or otherwise control the attribute data. For instance, the user may remove undesired attribute data via the functionality provided by the management module 230. In a further instance, the user may specify permissions for portions of the attribute data using the functionality provided by the management module 230. The permissions may allow or prohibit certain access or uses for the attribute data (e.g., the permission may prohibit access to the attribute data by third parties). The user may grant various levels of access and abilities. In some example embodiments, the permissions may persist for a period of time, and after expiration of the time period, the management module 230 may revoke the permissions.

In further example embodiments, the management module 230 may request consent from the user to access portions of the attribute data or to request permission for certain uses of the attribute data. For example, the management module 230 may request consent from the user to allow third parties to access portions of the attribute data. The management module 230 may request a variety of other consents associated with various actions corresponding to the attribute data.

In still further example embodiments, the management module 230 may provide functionality to allow third parties to access the attribute data or the user characteristics. For example, the management module 230 may provide a set of APIs that may be invoked by third parties to access the attribute data or the user characteristics. As discussed above, in some example embodiments, the management module 230 may determine permission or consent of the user prior to providing access to the attribute data.

Referring now to FIG. 2B, the analysis module 250 in the visualization system 152 may perform various analyses to facilitate the functionality described herein. For example, the analysis module 250 may determine satisfaction of a reward criteria associated with the attribute data. In this example, the reward criteria may include a fitness goal and the analysis module 250 may determine whether the user has satisfied the fitness goal based on an analysis of the attribute data. Many other rewards and analyses may be performed by the analysis module 250.

The commerce module 255 may identify items from an e-commerce platform (e.g., the publication system 142). The items (e.g., item listings on an e-commerce website) are intended to include products, services, activities, and the like. The commerce module 255 may also retrieve item data associated with the identified items such as item price, seller, item location, seller location, item images, item description, and so on. In some example embodiments, the commerce module 255 may facilitate the purchase, by the user, of the identified items.

The visualization module 260 may generate a visualization based, at least in part, on the attribute data. The visualization may be representative of the attribute data. For example, the visualization module 260 may generate an avatar that is representative of the attribute data. For example, the attribute data may indicate demographic data corresponding to the user such as gender, age, height, and so on. The visualization module 260 may generate the avatar based on the demographic data such as an avatar of the same gender and similar age, height, and so forth. The presentation module 210 may subsequently cause presentation of the generated visualization to the user.

Figure 3:
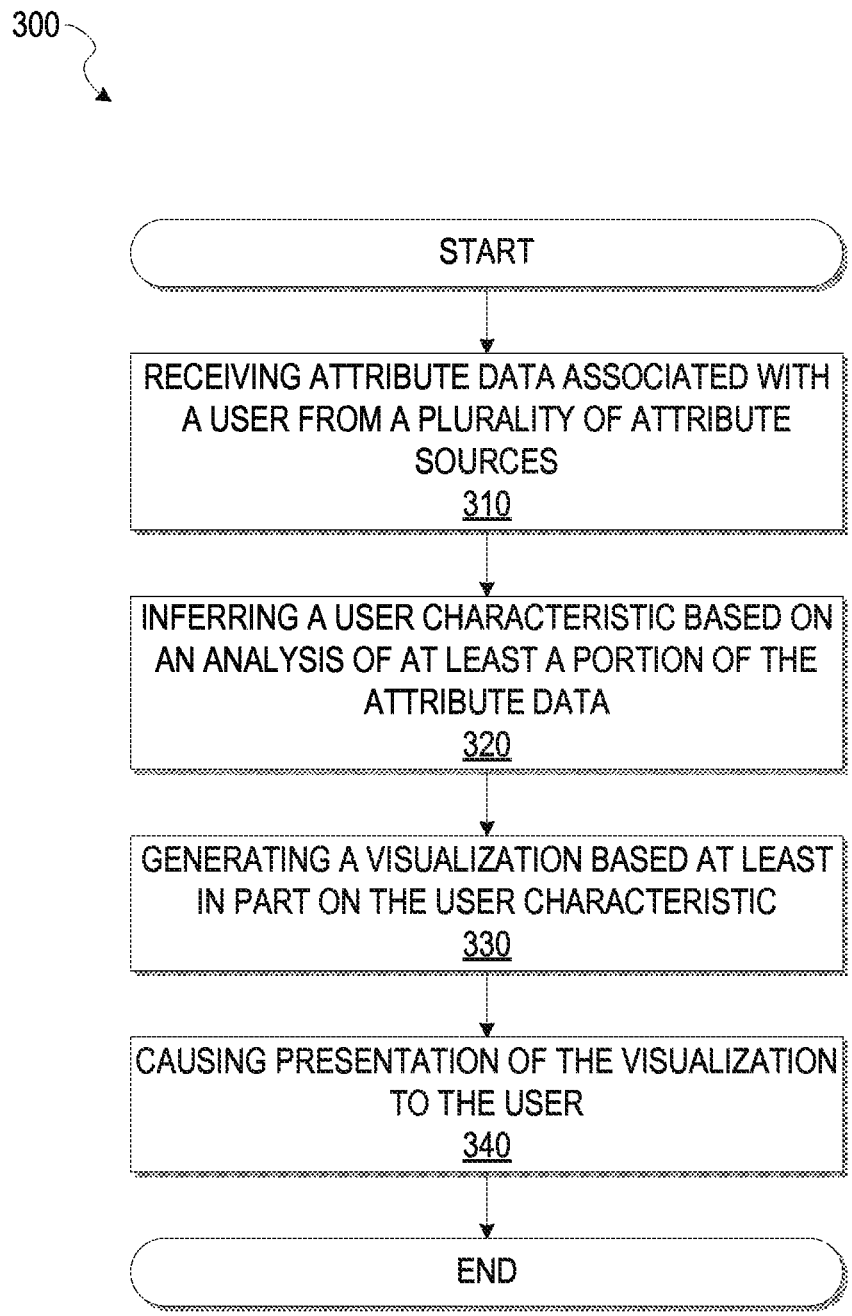
FIG. 3 is a flow diagram illustrating an example method for generating a visualization, according to some example embodiments.

FIG. 3 is a flow diagram illustrating an example method 300 for generating the visualization, according to some example embodiments. The operations of the method 300 may be performed by components of the data mesh system 150 and the visualization system 152. At operation 310, the attribute module 220 may receive the attribute data associated with the user from a plurality of attribute sources. As will be discussed in connection with FIGS. 12 and 13, the attribute data may be received from a broad spectrum of attribute sources (e.g., devices, sensors, servers, databases, and other sources). Additionally, the attribute module 220 may receive the attribute data via many pathways resulting from an assortment of configurations of the attribute sources as further discussed in connection with FIGS. 11A and 11B. In an example embodiment, the attribute module 220 may receive the attribute data directly from the attribute sources. In other example embodiments, the attribute module 220 may receive the attribute data from a central device that receives attribute data from a plurality of user devices. In still other example embodiments, various user devices may be communicatively coupled in a decentralized device-to-device mesh and the attribute module 220 may receive the attribute data corresponding to a particular device in the mesh from any of the devices in the mesh. The attribute module 220 may receive the attribute data from the attribute sources in many other configurations including various suitable combinations of configurations.

In various example embodiments, the attribute module 220 may store the attribute data in association with the user (e.g., indexed based on a user identifier) for subsequent analysis. The attribute module 220 may store the attribute data in a storage device such as the database(s) 126, for example. The attribute module 220 may access the stored attribute data using a variety of search or find schemes. For instance, the attribute data associated with a particular user may be accessed using a user identifier that corresponds to the particular user. It will be noted that the collective, aggregated attribute data may be referred to as a "data mesh."

In various example embodiments, at least a portion of the attribute data may include real-time data or near real-time data. The term "real-time data," as used herein, is intended to include data associated with an event currently happening. For example, the real-time data may include user input data or sensor data communicated to the attribute module 220 after a delay interval (e.g., due to transmission delay or other delays such as being temporarily stored at an intermediate device) between capturing the data and the attribute module 220 receiving the data.

At operation 320, the characteristic module 225 may infer or measure directly a user characteristic or multiple user characteristics based on an analysis of at least a portion of the attribute data. In some example embodiments, the characteristic module 225 may store the inferred user characteristics for subsequent analysis, for example, in a storage device such as database(s) 126. The characteristic module 225 may infer a vast spectrum of the user characteristics from the attribute data. A few specific examples of user characteristics may include demographic data (e.g., age, gender, marital status, number of children), user preferences (e.g., being a morning person, favorite locations, enjoying spicy food), idiosyncrasy (e.g., being forgetful such as draining the battery on a mobile device or being impatient such as a line breaker that will leave a store if the line is too long), qualities (e.g., being athletic, being tall, having a large vocabulary), personality traits (e.g., being a risk taker), actions, activities (e.g., working for a non-profit), attitudes, habits (e.g., being a coffee drinker), behaviors, beliefs, biases, demeanor, and physical characteristics of the user (e.g., height, weight, garment sizes, eye color, hair color). The specificity of the characteristics may range from very narrow (e.g., drinks a particular brand of soda) to very broad (e.g., being generally philanthropic). To illustrate inferring the user characteristic from the attribute data by way of example, the attribute data may include user location data that may indicate frequent visits to a local school, local soccer fields, and the like. In this example, the characteristic module 225 may infer that the user has children based on the types of locations the user may be frequently visiting.

In some instances, the characteristic module 225 may perform varying degrees of inferential analysis of the attribute data to derive the user characteristics. For example, the characteristic module 225 may infer the user's wake-up time based on user device activity or other activity (e.g., connected alarm clock settings, logins to accounts, and various other user activities that may indicate a wake-up time). In this example, the characteristic module 225 may infer a particular user characteristic that may be of a larger inferential jump such as the user being a morning person or a person that likes to sleep in. The degree of inferential jump may be configurable. In some example embodiments, the characteristic module 225 may employ various techniques to minimize or otherwise control incorrect inferences (e.g., machine learning, other learning algorithms).

In further example embodiments, the characteristic module 225 may learn or evolve as more of the attribute data is received (e.g., via machine learning techniques or other learning algorithms). For example, the attribute data may include location data of the user. The characteristic module 225 may infer a favorite location of the user based on a pattern (e.g., frequently visited locations) in the location data. However, the characteristic module 225 may subsequently receive employment data of the user that may indicate a current employer including an employer location. The characteristic module 225 may learn, update, or otherwise adapt to account for the new attribute data. Thus, in this example, the characteristic module 225 may not infer a favorite location of the user if the location is a work location of the user. In some instance, the user may provide input directly (e.g., via a user interface configured to receive inferential guidance from the user) to facilitate the characteristic module 225 in inferring characteristics from the attribute data (e.g., user input indicating that a particular inferred characteristic is incorrect or providing input to be used as a basis for future inferences).

In other instances, the characteristic module 225 may perform very little or no analysis to derive the user characteristic from the attribute data. For example, the attribute data may include an alarm time setting from a connected alarm clock (e.g., a smart phone with an alarm clock app). The alarm time setting may directly indicate a wake-up time. Since the attribute data directly relates to a particular user characteristic, the characteristic module 225 need not perform analysis to derive the user characteristic.

In some example embodiments, the user characteristic may comprise predefined characteristics or dynamically determined characteristics. For instance, a particular set of characteristics may be predefined (e.g., work location, home location, marital status, socio-economic level). The characteristic module 225 may determine that particular predefined characteristics are associated with the user based on an analysis of the attribute data. In other instances, the characteristic module 225 may dynamically determine characteristics based on the attribute data. For example, the attribute data may indicate that the user owns a particular exotic pet. Although there may not be a predefined characteristic associated with the particular exotic pet, the characteristic module 225 may determine the user characteristic of owning an exotic pet from the attribute data.

In a specific example, the characteristic module 225 may infer the user's physical dimensions based on the attribute data that may include purchase history. For instance, the characteristic module 225 may use demographic information such as age, gender, or location to filter clothing purchases included in the purchase history (e.g., filtering to identify clothing purchase intended for the user). Based on the filtered clothing purchase history, the characteristic module 225 may identify the user's physical dimensions based on the garment sizes of the clothing purchases. In another specific example, the characteristic module 225 may infer the user's fitness level based on fitness tracking software included in a mobile device of the user. Thus, in these specific examples, the characteristic module 225 may infer various physical characteristics or traits of the user based on the attribute data.

At operation 330, the visualization module 260 may generate a visualization based, at least in part, on the user characteristic. In some cases, the term "visualization" as used herein is intended to include visual and non-visual components of a presentation (e.g., an animation including audio cued to the animation). The term "visualization" is also intended to include static images, animations, and other forms of visual presentation.

In an example embodiment, the visualization may comprise a chart or graph that may indicate a metric associated with the attribute data. For instance, the metric associated with the attribute data may be a completeness metric that indicates completeness of the attribute data associated with the user. That is to say, the completeness metric may indicate a quantity of attribute data versus a goal quantity of attribute data or attainable quantity of attribute data (e.g., the completeness metric may indicate a quantity of the attribute data associated with the user is sixty percent of the way to an goal quantity of attribute data).

In another example embodiment, the visualization may comprise an avatar that is representative of the user. For example, the avatar may be a person like animation or image that may be intended to represent the user. The avatar does not necessarily need to resemble the user's physical qualities or personality traits. However, in some example embodiments, the avatar may be intended to include qualities or traits that are similar or the same as qualities or traits of the user. In other words, the avatar may be visually analogous to the user. The visualization module 260 may determine an avatar trait based, at least in part, on the inferred user characteristic and include the avatar trait when generating the avatar. In some example embodiments, the user characteristic may comprise a physical characteristic of the user and the avatar trait may comprise a representation of the physical characteristic. For example, the characteristic module 225 may infer various user characteristics such as physical dimensions of the user, demographic information, personality traits and the like. In this example, the physical dimensions may indicate a person who may be six feet tall, the demographic information may indicate a gender of female and an age of twenty two, and the personality traits may indicate an outlandish tendency. As such, the avatar in this example may resemble a six foot tall woman and may include apparel that is congruent with having an outlandish tendency. Thus, the avatar may visually exemplify various characteristics of the user.

In various example embodiments, the visualization module 260 may employ a variety of schemes and techniques to determine an avatar trait based, at least in part, on the inferred user characteristic. In an example embodiment, the analysis module 250 may identify similar users that are similar to the user based on a variety of factors. In some example embodiments, the analysis module 250 may access the attribute data or stored user characteristics corresponding to a plurality of other users. For example, the analysis module 250 may identity the similar users from among the plurality of other users that are similar to the user based on the inferred users characteristics of the user and respective user characteristics of the plurality of other users. The analysis module 250 may correlation, match, or otherwise compare the inferred user characteristics with respective user characteristics of the plurality of other users to identity the similar users. In various example embodiments, the analysis module 250 may identify the similar users based on same or similar demographic data (e.g., same or similar age, gender, location, etc.), same or similar user characteristics (e.g., same or similar brand purchases), same or similar attribute data, and so on. For instance, the analysis module 250 may correlated the inferred user characteristics with respective user characteristics of other user to identify the similar users.

Subsequent to the analysis module 250 identify the similar users, the visualization module may extract common characteristics from among the identified similar users. The visualization module 260 may generate the visualization based on the extracted common characteristics. In the example above, the analysis module 250 may identify particular similar users that are associated with being outlandish. Continuing with this example, the visualization module 260 may extract the common characteristics (e.g., a particular style of clothing or brand) from among the identified plurality of users. For instance, the common characteristic may be wearing a particular clothing color, style, brand, and so on. The visualization module 260 may generate or render the avatar to include a particular avatar trait that corresponds to the common characteristic (e.g., wearing a particular clothing brand).

In further example embodiments, the visualization module 260 may apply weighting the inferred user characteristics and the extracted common characteristics in various schemes to generate the visualization based on the inferred user characteristics or the extracted common characteristics. For example, a particular user characteristic that may be inferred from particular attribute data that correspond to a time further in the past may be weighted less heavily than a particular user characteristics interred from particular attribute data that is more recent. The reasoning being that more recent data may be more relevant or pertinent to the objective of generating the visualization in a manner that accurately reflects the user or the attribute data. The visualization module 260 may apply weighting using many other schemes and the above is merely a non-limiting example.

In still further example embodiments, the visualization module 260 may generate the visualization based, at least in part, on the real-time data included in the attribute data. For example, the characteristic module 225 may infer the user characteristics based, at least in part, on the real-time data and the visualization module 260 may generate the visualization based on the user characteristics inferred from the real-time data. Thus, the visualization may be reflective of a current status of the user. In a specific example, the characteristic module 225 may infer that the user may currently be jogging vigorously at a park. The visualization module 260 may, for example, generate the visualization, such as the avatar, to include a feature of perspiration indicative of the user currently performing a vigorous physical activity. Thus, the visualization may be representative of a real-time status of the user. In a further example, the characteristic module 225 may infer an outfit the user is currently wearing (e.g., inferred from attribute data that may include detections from smart tags embedded into the user's clothing) and the visualization module 260 may generated the avatar to include a representation of the inferred outfit.

At operation 340, the presentation module 210 may cause presentation of the visualization to the user. For example, the visualization may comprise an avatar and the presentation may be displaying the avatar on a screen. The presentation module 210 causing presentation of the visualization may include communicating the visualization, or instructions to present the visualization, to a device of the user operable to present the visualization to the user. In further example embodiments, the presentation module 210 may cause the presentation of the visualization to other users. For instance, the user may be associated with a profile and viewers of the user's profile may also view the visualization. In other example embodiments, the user may be associated with contact users that have a connection with the user such as a social media based relationship. In this example embodiment, the visualization may be presented to the contact users.

Figure 4:
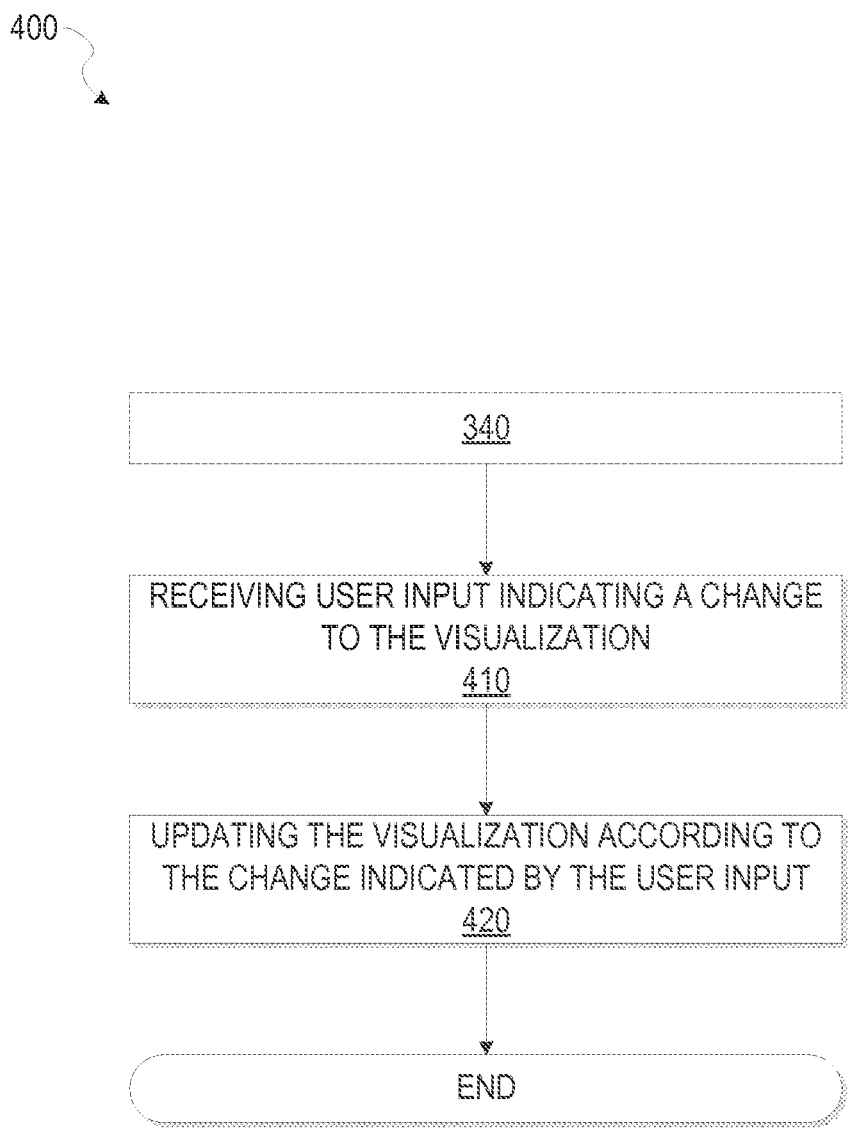
FIG. 4 is a flow diagram illustrating further example operations of the method of FIG. 3, according to some example embodiments.

FIG. 4 is a flow diagram illustrating further example operations 400 of the example method 300 of FIG. 3 according to some example embodiments. Subsequent to the operation 340, at operation 410, the presentation module 210 may receive user input indicating a change to the visualization. For example, the user input may indicate that the visualization is based on user characteristics or attribute data that is not reflective of the user. In this example, the visualization may be an avatar and the physical characteristics of the avatar may not be reflective of the user (e.g., the avatar is too short as compared to the user).

At the operation 420, the visualization module 260 may update the visualization according to the change indicated by the user input. In the example above, if the user input indicated that the avatar was too short, the visualization module 260 may generate or render the avatar with a taller height.

In further example embodiments, the attribute module 220 may update or modify the attribute data according to the user input. For instance, if the user input indicates demographic data (e.g., age) other than that currently associated with the user, the attribute module 220 may update the demographic information according to the user input.

In still further example embodiments, the characteristic module 225 may infer the user characteristics based on an analysis of the attribute data and the user input. For instance, if the user input indicates a particular clothing style, color, brand, and so forth, the characteristic module 225 may use that user input as a basis for inferring the user characteristics in conjunction with the attribute data.

Figure 5:
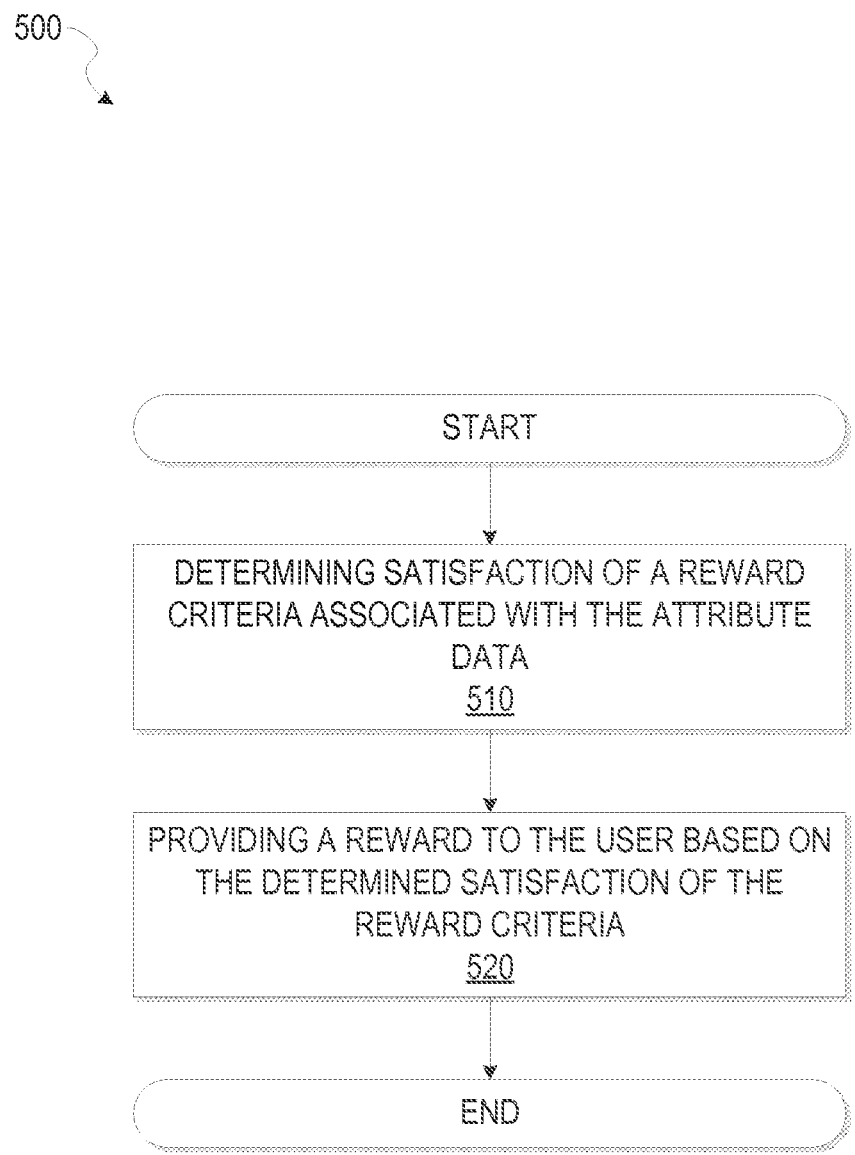
FIG. 5 is a flow diagram illustrating an example method for determining satisfaction of reward criteria, according to some example embodiments.

FIG. 5 is a flow diagram illustrating an example method 500 for determining satisfaction of a reward criteria and providing a reward to the user according to some example embodiments. The operations of the method 500 may be performed by components of the data mesh system 150 and the visualization system 152. At operation 510, the analysis module 250 may determine satisfaction of the reward criteria associated with the attribute data. The reward criteria may include a variety of criterion.

In an example embodiment, the reward criteria may include a criterion based on the completeness metric. In an example embodiment, the analysis module 250 may determine the completeness metric based on an analysis of the attribute data. The completeness metric may indicate a quantity of attribute data available to the data mesh system 150. In some example embodiments, the completeness metric may indicate the quantity of attribute data in comparison to a goal quantity of attribute data or attainable quantity of attribute data (e.g., the completeness metric may indicate a quantity of the attribute data associated with the user is sixty percent of the way to a goal quantity of attribute data). For instance, the user may have provided the attribute data, permission to access portions of the attribute data, or consent to access portions of the attribute data via the management module 230 (e.g., the user may have provided permission to the attribute management module 230 to allow the attribute module 220 to access mobile sensor data but not social networking data). In this instance, the completeness metric may indicate that portions of the attribute data may not be available to the attribute module 220. The analysis module 250 may determine satisfaction of the criterion based on the completeness metric if the completeness metric exceeds a threshold. The threshold may be predefined or dynamically determined by the analysis module 250 based on various statistical analyses.

In a further example embodiment, the completeness metric may be associated with a specified type of attribute data. In this further example embodiment, the analysis module 250 may determine the criterion based on the completeness metric may be satisfied if the user provides the specified type of attribute data or permission to access the specified type of attribute data.

In another example embodiment, the reward criteria may include a criterion based on a quality metric. In this example embodiment, the analysis module 250 may determine the quality metric based on an analysis of the attribute data. The quality metric may indicate a relevance or pertinence of the attribute data. For instance, older attribute data may be less relevant than newer attribute data. In an example embodiment, the quality metric may be higher for new attribute data and lower for older attribute data. Thus, a particular user associated with attribute data that is constantly updated may be associated with a higher quality metric. The analysis module 250 may determine satisfaction of the reward criteria that includes the criterion based on the quality metric based on the quality metric exceeding a threshold. That is to say, the analysis module 250 may determine satisfaction of the reward criteria that includes a particular criterion based on the quality metric by providing recent data, for example. The threshold may be predefined or dynamically determined by the analysis module 250 based on various statistical analyses.

In yet another example embodiment, the reward criteria may include a criterion associated with completing a task. For instance, the task may include the user recommending or communicating (e.g., email, text message) to other users regarding a product or application. The presentation module 210 may facilitate the user in performing the task (e.g., automatically determining available contact that may be contacted and providing a predetermined message that may be sent via a user interface provided by the presentation module 210). In other instances, the task may include a specified goal. In this instance, the goal may, for example, be a fitness goal such as a number of steps taken in a day (e.g., as determined a pedometer app executing on a mobile device of the user). Continuing with this instance, the analysis module 250 may determine satisfaction of the reward criteria including a criterion based on a number of steps taken if the user exceeds a threshold number of steps.

In further example embodiments, the analysis module 250 may determine satisfaction of the reward criteria including various criteria (e.g., criterion based on the completeness metric or the quality metric) by comparing metrics associated with the user to other users. As described above, the analysis module 250 may identify the similar users that are similar to the user based on a variety of factors. The analysis module 250 may determine satisfaction of the reward criteria by comparing the various metrics associated with the user to the various metrics associated with the similar users. In a specific example, the similar users may include users that may have the same or similar demographic data (e.g., age, gender, location). Among these similar users, the analysis module 250 may determine an average completeness metric or another statistic-based value. The analysis module 250 may compare the completeness metric of the user to the average completeness metric or another statistic based value to determine satisfaction of a particular criterion associated with the completeness metric of the user (e.g., the user may satisfy the reward criteria by being above average as compared to similar users). Similarly, the analysis module 250 may compare a fitness goal of a user to the similar users that may be of a similar fitness level to the user. The analysis module 250 may employ many other comparisons of the similar users or other users to determine satisfaction of the reward criteria. Thus, in some example embodiments, the analysis module 250 may determine satisfaction of the reward criteria based on the attribute data associated with the identified similar users.

At the operation 520, the analysis module 250 may provide a reward to the user based on the determined satisfaction of the reward criteria. The reward may include additional visualization features or functions. For instance, the reward may include providing the user the ability to further customize the visualization (e.g., modify apparel of the avatar). In another instance, the reward may provide the user with additional features such as the ability to share the visualization with other users. The reward may include many other features and functions related to the visualization.

In further example embodiments, the reward may include a coupon, deal, or other incentive. The reward may incentivize the user to provide consent, permission, or access to additional attribute data, provide higher quality more relevant attribute data, complete various marketing tasks, complete various goals (e.g., a fitness goal), and so forth.

Figure 6:
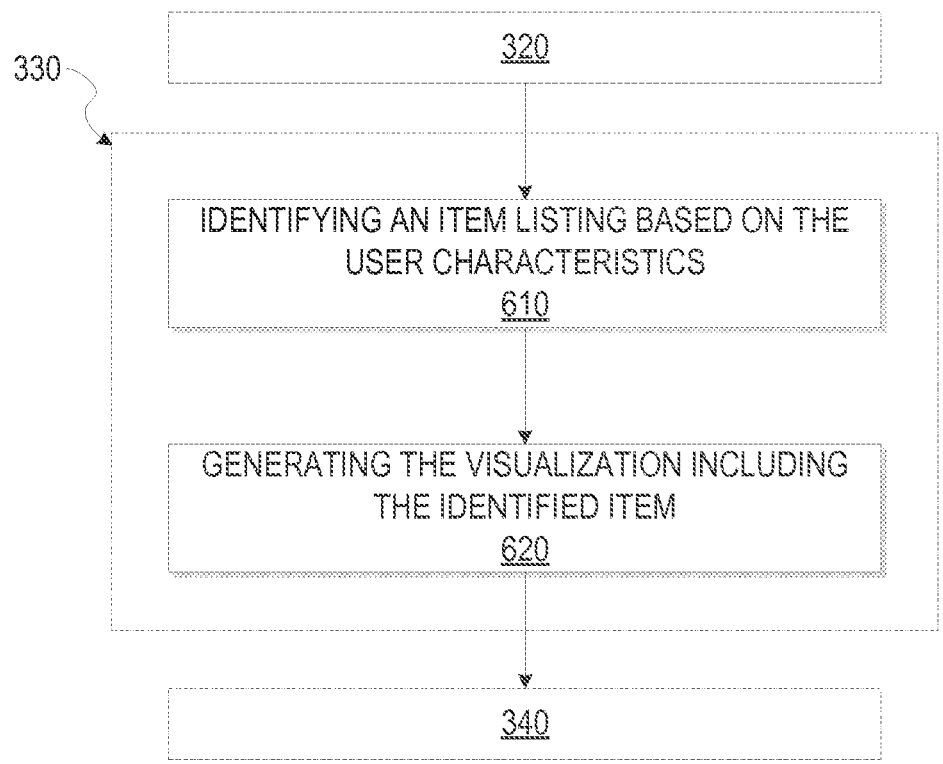
FIG. 6 is a flow diagram illustrating further example operations of the method of FIG. 3, according to some example embodiments.

FIG. 6 is a flow diagram illustrating additional operations of the method 300 according to some example embodiments. Subsequent to the operation 320, at the operation 330 the visualization module 260 may generate the visualization based at least in part on the user characteristics. In addition, at operation 610, the commerce module 255 may identify an item listing based on the user characteristics. For instance, the user characteristics may indicate the user's preferences for clothing, electronics, and so on. Further, the attribute data may include purchase history data that the commerce module 255 may use to determine products already owned by the user. By analyzing this information, the commerce module 255 may identify an item listing of interest to the user (e.g., an item listing on an e-commerce website). The commerce module 255 may employ a variety of schemes and techniques using the user characteristics and the attribute data to identify the item listing.

At the operation 620, the visualization module 260 may generate the visualization including the identified item associated with the identified item listing. For example, the visualization generated by the visualization module 260 may include the avatar that may be representative of the user. In this example, the visualization module 260 may generate the avatar to include the avatar wearing or using a suitable item associated with the identified item listing. The commerce module 255 may access item data associated with the identified item associated with the identified item listing. For example, the commerce module 255 may access the item data that may include images of the item, physical dimensions of the item (e.g., garment sizes), and so forth. Based on the item data, the visualization module 260 may generate the visualization to include a representation of the identified item. The representation may be similar to the item in that it may include similar characteristics to the identified item. For example, the identified item may be a particular piece of apparel. In this example, the visualization module 260 may render a representation of the piece of apparel that is of the same or similar dimensions, color, pattern, and so forth.

In further example embodiments, the item associated with the identified item listing may be highlighted or otherwise emphasized in the rendering of the avatar. In some example embodiments, the user may interact with the generated item rendering associated with the identified item listing included in the avatar (e.g., interacting with the item may cause recommendation for sale of the item listing).

Figure 7:
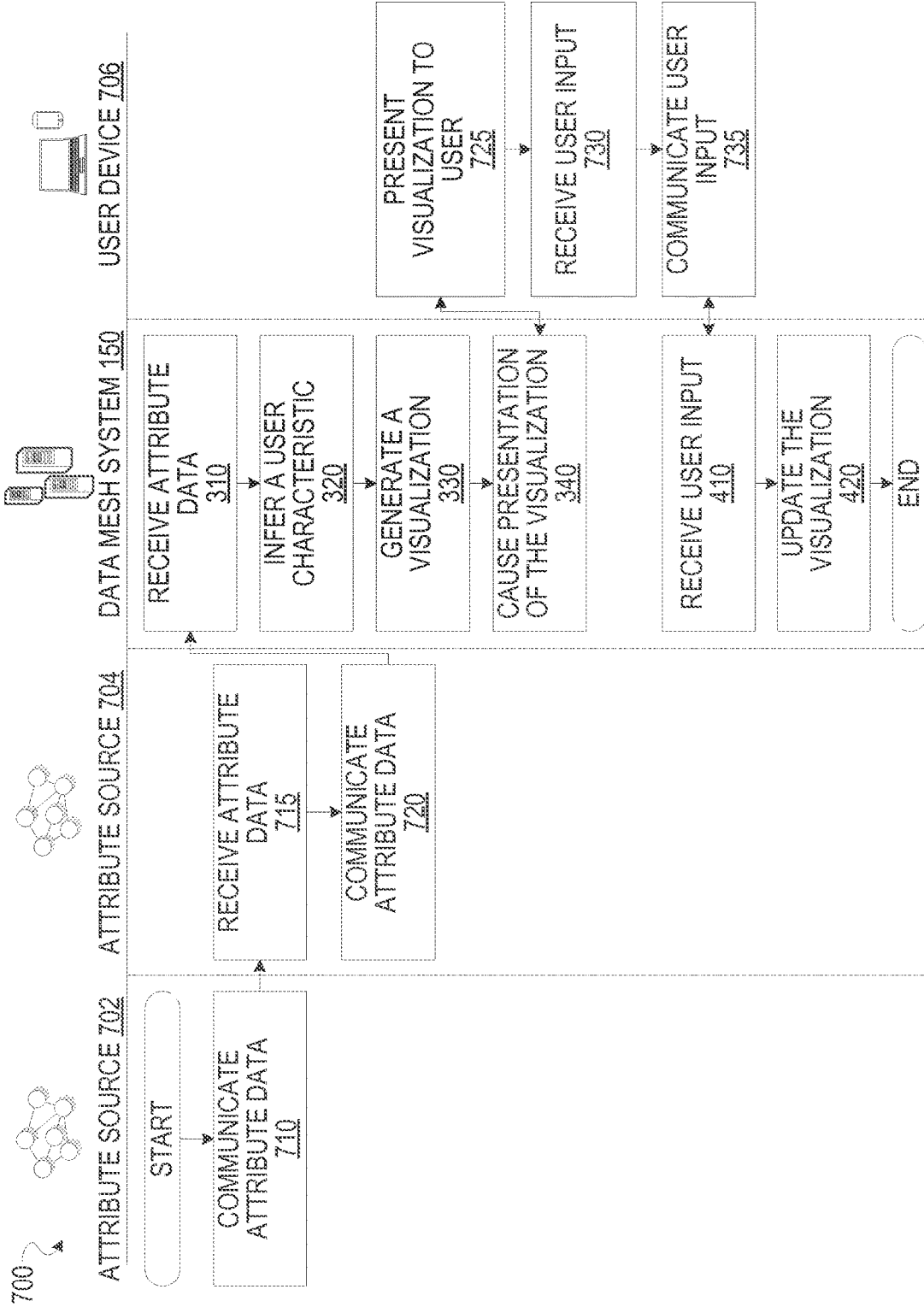
FIG. 7 is a flow diagram illustrating various communications to facilitate the method of FIG. 3, according to some example embodiments.

FIG. 7 is a flow diagram illustrating an example method 700 for generating the visualization based on the attribute data according to some example embodiments. The operations of the method 700 may be performed by components of the data mesh system 150 and the visualization system 152. In an example, embodiment, at operation 710, attribute source 702 may communicate the attribute data to the attribute source 704. At the operation 715, the attribute source 704 may receive the attribute data from the attribute source 702. At operation 720, the attribute source 704 may communicate the attribute data to the data mesh system 150. As discussed above in connection with FIG. 3, at the operation 310, the data mesh system 150 may receive the attribute data from the attribute source 704. In this example embodiment, the attribute data may be exchanged between the attribute source 702 and the attribute source 704. In this way, the data mesh system 150 may access various attribute data corresponding to a particular attribute source without directly communicating with the particular attribute source.

As discussed above in connection with FIG. 3, at the operation 320, the characteristic module 225 may infer a user characteristic. At the operation 330, the visualization module 260 may generate the visualization based, at least in part, on the user characteristic. At the operation 340, the presentation module 210 may cause presentation of the visualization to the user. The presentation module 210 may cause presentation of the visualization by communicating the visualization to the user device 706. At operation 725, the user device 706 may present the visualization to the user. For example, the user device 706 may be a mobile device of the user and the presentation may be displaying the visualization on a screen of the mobile device. Subsequent to presenting the visualization to the user, at operation 730, the user device 706 may receive user input from the user. In some example embodiments, the user input may result from an interaction with the presented visualization. At the operation 735, the user device 706 may communicate the user input to the data mesh system 150. For example, the user input may be received by the presentation module 210 of the data mesh system 150.

As discussed above in connection with FIG. 4, at the operation 410, the presentation module 210 may receive the user input indicating a change to the visualization. At the operation 420, the visualization module 260 may update the visualization according to the change indicated by the user input. Thus, FIG. 7 has shown various communications or interactions between devices according to some example embodiments.

FIGS. 8, 9, 10A, and 10B depict example user interface for presenting the visualization to the user. Although FIGS. 8, 9, 10A, and 10B depict specific example visualization and user interface elements, these are merely non-limiting examples and many other alternate visualization and user interface elements may be generated by the presentation module 210 and presented to the user. It will be noted that alternate presentations of the displays of FIGS. 8, 9, 10A, and 10B may include additional information, graphics, options, and so forth; other presentations may include less information, or may provide abridged information for easy use by the user.

Figure 8:
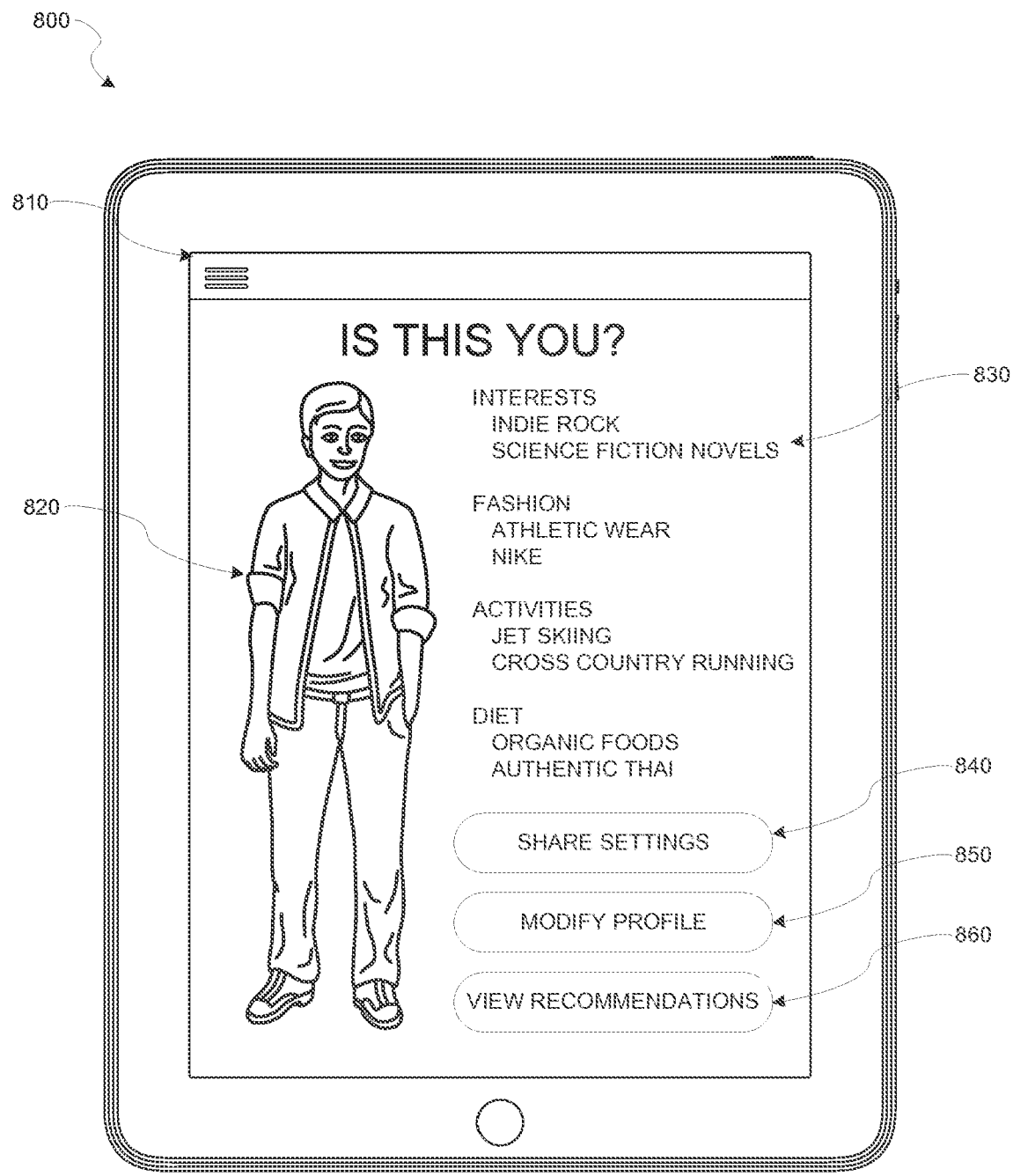

FIG. 8 depicts an example device 800 displaying an example user interface 810 to present the visualization to the user. In an example embodiment, the visualization may be an avatar 820 that is based on the inferred user characteristics. In a specific example, the approximate physical size of the user may be derived from purchase history data such as clothing sizes, user input (e.g., user input to a fitness app that requests the user's size to make various calculations), and so on. The user characteristics may include style characteristics extracted, derived, or inferred from the attribute data (e.g., type of clothing purchased, types of activities the user engages in, and so on). In other example embodiments, the avatar 820 may be used as a virtual fitment gauge to determine how particular apparel may appear on the person. Although the visualization of FIG. 8 depicts the avatar 820, many other varieties of visualization may be rendered by the visualization module 260 and presented to the user by the presentation module 210.

In some example embodiments, the user may have provided interests and other information to the data mesh system 150, as depicted by user interface element 830. In some example embodiments, the user may modify access permission to the user information, for example, by activating user interface element 840. The user may also edit or modify the attribute data, for example, by activating user interface element 850. In further example embodiments, the user may be provided with recommendations that are based on an analysis of the attribute data or the user characteristics. For example, activating user interface element 860 may display various personalized recommendations.

Figure 9:
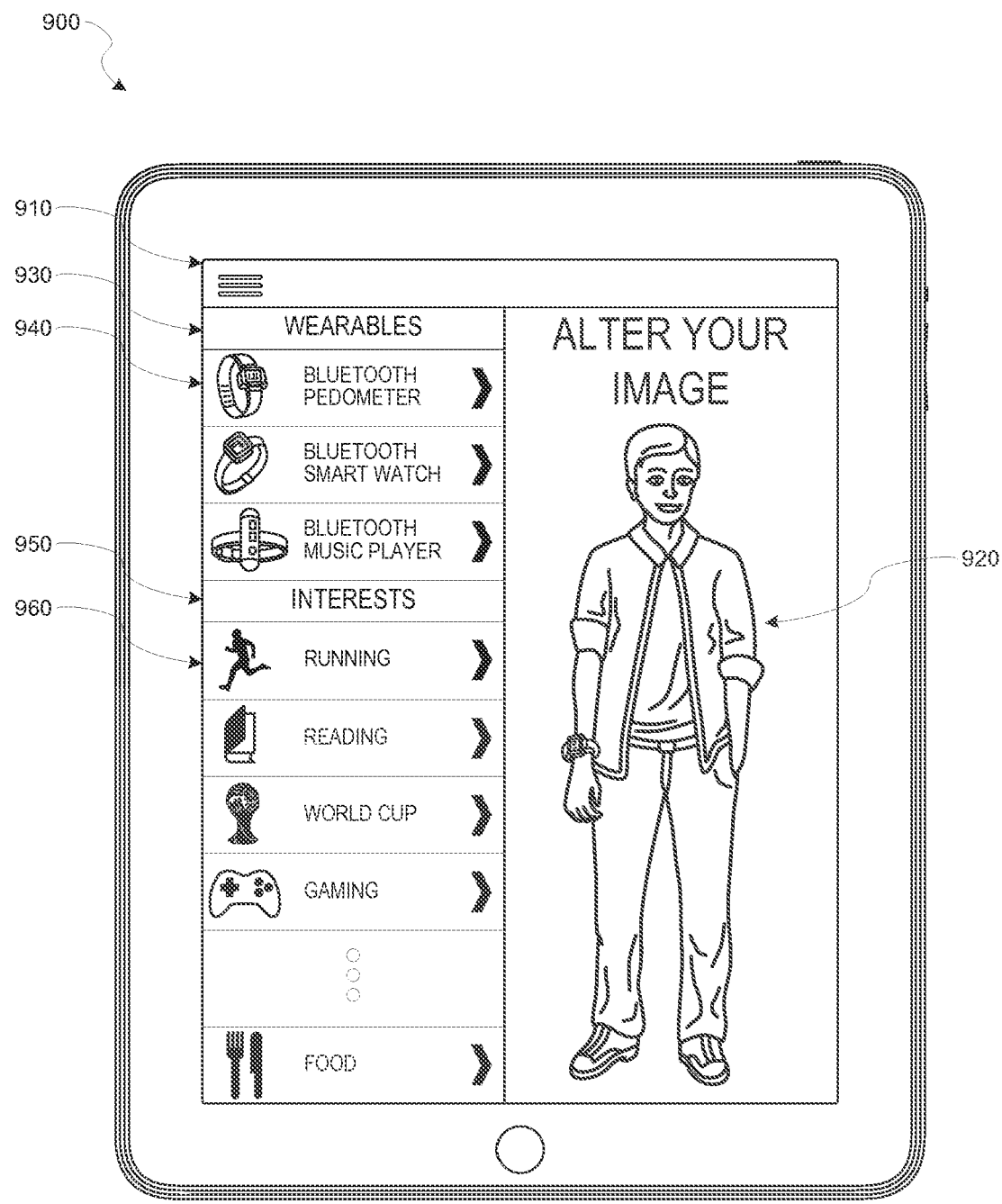

FIG. 9 depicts an example device 900 displaying an example user interface 910 that may present the visualization to the user. The example user interface 910 may include recommended items or allow the user to provide the user input to alter the visualization. For example, user interface element 930 may include a plurality of recommended items such as user interface element 940. The user may activate (e.g., dragging a user interface element onto the area occupied by the avatar 940) a particular recommended item to indicate an interest in the particular recommended item. The visualization may be updated or otherwise modified responsive to the user activating the particular recommended item. For example, the recommended item may be visually incorporated into the visualization such as the avatar 920 may be shown to wear the recommended item when suitable. In further example embodiments, the user may provide indications interests and other information. For instance, user interface element 950 may include a plurality of user interests such as interest 960. In an example embodiment, the user may select an interest from a plurality of interests. Based on the selected interest, the visualization module 260 may modify the visualization. In still further example embodiments, the characteristic module 225 may incorporate the selected interest into the analysis to determine the user characteristics.

FIG. 10A depicts an example device displaying an example user interface 1010 to present the visualization to the user. Similarly, FIG. 10B depicts an example device displaying an example user interface 1050 to present the visualization to the user. In an example embodiment, as more attribute data is provided to the data mesh system 150, the more detailed and accurate the visualization module 260 may render the visualization representative of the attribute data. For example, the user may be a college aged male with an athletic build. In this example, avatar 1020 of FIG. 10A may be a less detailed and less accurate representation of the user than avatar 1060 of FIG. 10B. The avatar 1020 may be an initial representation of the attribute data and the avatar 1060 may be a subsequent representation of the attribute data after the data mesh system 150 receives more attribute data from the user allowing the visualization system 152 to more accurately represent the user.

Figure 11B:
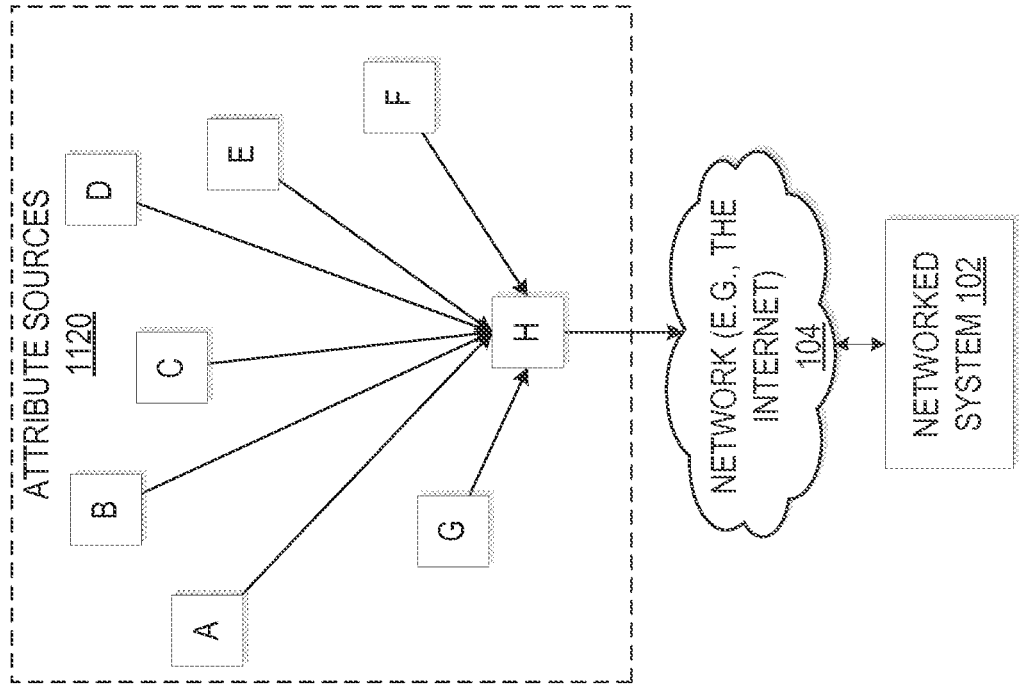
FIGS. 11A and 11B depict example configurations for communicatively coupling attribute sources, according to some example embodiments.
Figure 11A:
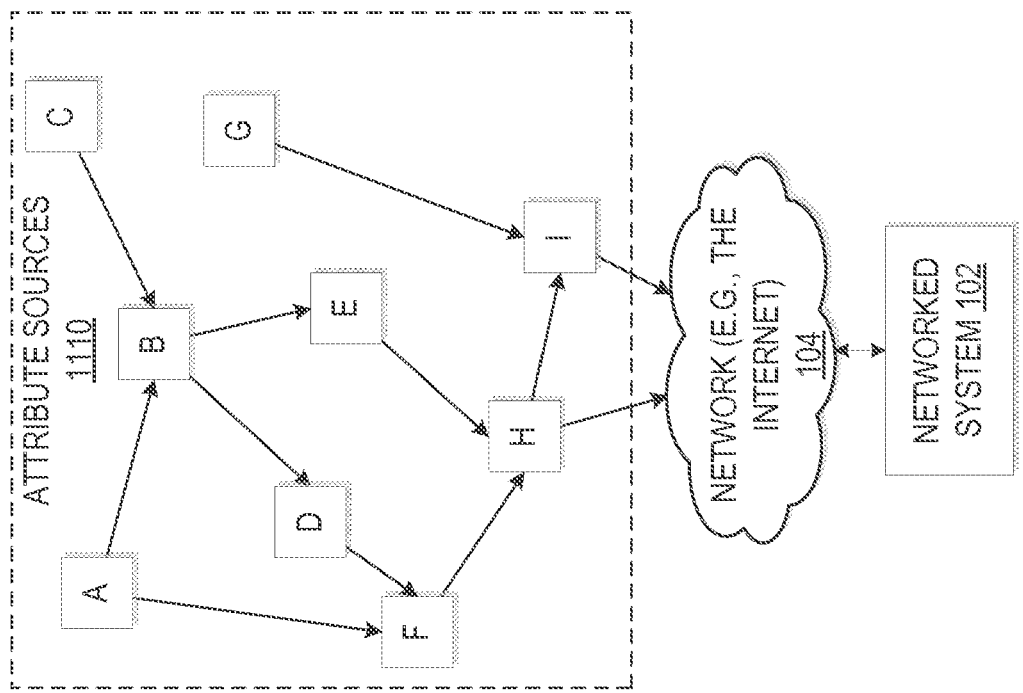

FIGS. 11A and 11B depict example configurations for communicatively coupling attribute sources, according to some example embodiments. The example embodiments described herein may access a vast and rich "Internet of Things" (IoT) dataset that is predominantly provided via communicatively connected, interconnected, or otherwise communicatively coupled machines and devices that may include a multitude of sensors. In example embodiments, devices and machines that provide the attribute data, such as the attribute sources, may be communicatively coupled in many different configurations. For instance, each attribute source may be communicatively coupled to the networked system 102 independently to provide the networked system 102 access to the attribute data corresponding to each of the communicatively coupled attribute sources. FIGS. 11A and 11B depict alternative example attribute source configurations. It will be appreciated that FIGS. 11A and 11B are merely non-limiting examples of attribute source configurations and many other configurations or suitable combinations of configurations may be employed.

FIG. 11A depicts an example embodiment that may include attribute sources 1110 communicatively coupled in a decentralized device-to-device mesh. In this example embodiment, the attribute data corresponding to a particular device in the mesh may be received from any one or more of the devices in the mesh. For instance, the networked system 102 may access the attribute data corresponding to attribute source E via attribute source H or a combination of attribute sources H and I in FIG. 11A. In an example embodiment, the attribute source H or I may aggregate and store the attribute data corresponding to attribute sources A-F in FIG. 11A. In some example embodiments, the networked system 102 may access the attribute data associated with attribute source E by communicating with attribute source H or I in FIG. 11A.

FIG. 11B depicts another example embodiment that may include attribute sources 1120 communicatively coupled to a central attribute source (e.g., attribute source H in FIG. 11B). The networked system 102 may access the attribute data associated with attribute sources A-G via the central attribute source in FIG. 11B. In some embodiments, the central attribute source may aggregate and store the attribute data received or accessed from the attribute sources A-G and provide a centralized access point for the attribute data associated with all, or some, of the communicatively coupled attribute sources A-G in FIG. 11B.

Figure 12:
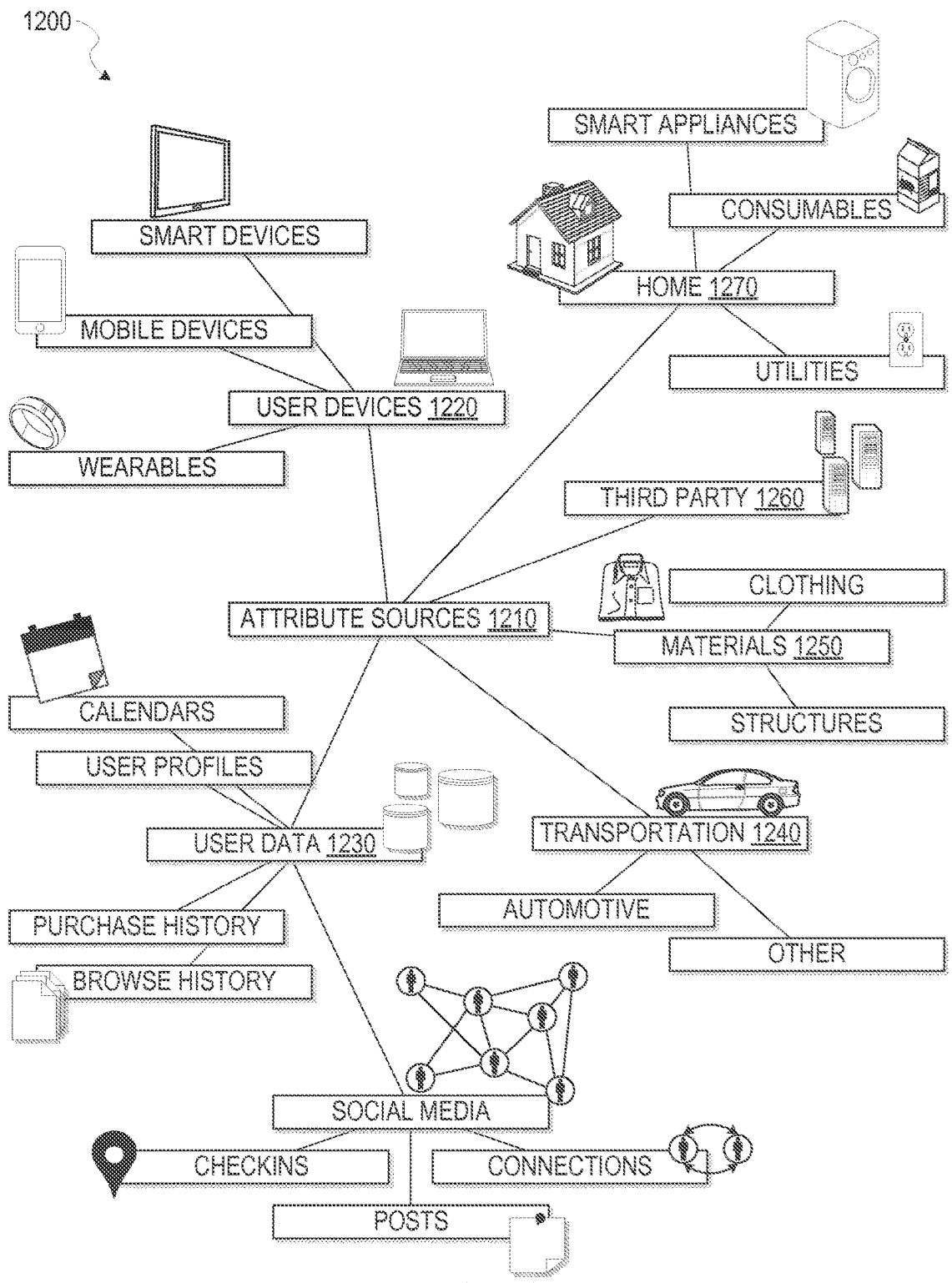
FIG. 12 depicts various example attribute sources, according to some example embodiments.

FIG. 12 depicts example sources 1200 including attribute sources 1210, according to some example embodiments. In various example embodiments, the attribute data may include data received, retrieved, or accessed from the attribute sources 1210. For example, the attribute sources 1210 may provide data including everything from a moisture level of a houseplant to a dribbling rhythm of a basketball. In some embodiments, the attribute data corresponding to the attribute sources 1210 may be received or accessed in real-time or near real-time. For instance, the attribute sources 1210 may communicate or otherwise provide access to the attribute data as it becomes available. In example embodiments, the attribute sources 1210 may include user device sources 1220, user data sources 1230, transportation sources 1240, materials sources 1250, third party sources 1260, home sources 1270, and a variety of other sources. As will be discussed in connection with FIG. 13 the attribute sources 1210 may be associated with a wide variety of sensors, gauges, measurement components, and other components.

In an example embodiment, the attribute data may include data corresponding to the user device sources 1220. The user device sources 1220 may include such non-limiting examples as a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), and other smart devices. As will be discussed further in connection with FIG. 13, the attribute data corresponding to the user device sources 1220 may include data associated with sensors, gauges, and other measurement components such as environmental sensor data (e.g., ambient temperature), biometric sensor data (e.g., heart rate), detection data (e.g., detection of a Near Field Communication (NFC) beacon), motion data (e.g., acceleration), position data (e.g., location as determined by a GPS of a mobile device), and so forth.

In further example embodiments, the attribute data corresponding to the user device sources 1220 may include data such as device type, device model, device name, a unique device identifier, and other device parameters. In some example embodiments, the device type data may provide a basis for an inference associated with the attribute data. For instance, if the device type data indicates that the device is a mobile device of the user, location data corresponding to the mobile device may indicate the location of the user. Similarly, if the device type is a media entertainment system, the attribute data corresponding to the media entertainment system may be associated with a home of the user.

The user data sources 1230 may include calendars (e.g., user calendar events such as birthdays, trips, exams), user profiles (e.g., demographic information such as age, gender, income level), purchase histories, browse histories (e.g., search terms), social media content (e.g., checkins, posts, connections), other user data (e.g., bookmarked websites, preferences or settings for various applications, application usage data such as time spent using a particular application), and the like. The attribute data corresponding to the user data sources 1230 may be stored, for example, by the user device sources 1220 (e.g., a mobile device that includes a mobile browser with browse history of the user), application server(s) 140 (e.g., payment history of the user stored in payment system(s) 144, user profiles stored by an e-commerce website), the third party server(s) 130 (e.g., social media data stored in a social networking service), and so on. For example, the attribute data corresponding to the user device sources 1220 may include device resource data. The device resource data may include files stored on the devices or metadata associated with the files. For instance, the device resources may include digital media files (e.g., MP3 formatted songs) or apps (e.g., pedometer app). The metadata associated with the device resources may include usage data such as number of times a song has been played, amount of time using a particular app, and so forth.

As cars and other forms of transportation become increasingly equipped with sensors and the ability to communicate, a vast amount of data may be provided by the transportation sources 1240. For example, the attribute data corresponding to the transportation sources 1240 may include acceleration data, velocity data, and other sensors data (e.g., brake pad wear data, gear shifting data). In this example, the attribute data corresponding to the transportation sources 1240 may provide indications of a user's driving patterns and styles (e.g., comes to a complete stop at a stop sign, speeds, or finicky use of the brakes).

The materials sources 1250, such as clothing and structures, are also increasingly gaining the ability to capture data. In various example embodiments, the attribute data may include data corresponding to the materials sources 1250. For example, clothing may be embedded with sensors to detect motion. Data from these sensors may provide indications of whether the user is agile or inactive. In another example, clothing may be embedded with biometric sensors that may provide continuous feed of biometric data corresponding to the user. The biometric data may provide indications of the user's health, athletic ability, and many other characteristics corresponding to the user. Similarly, structures may be equipped with sensors to passively or actively monitor the surrounding environment (e.g., street cameras, traffic cameras, and other sensors).

In example embodiments, the attribute data may include data associated with the third party sources 1260. The third party sources 1260 may also provide an abundance of data associated with the user. For instance, the attribute data may include data accessed from government websites or other public records that may provide criminal histories, civil citation histories, credit histories, or other publicly available information.

Nearly every facet of a smart home may be capable of providing data associated with the user. The attribute data may include data corresponding to the home sources 1270. For instance, the home sources 1270 may include smart appliances, consumables, utilities, and many other smart home devices. In a few specific instances, the attribute data may include consumable inventories and consumption rates of various consumable goods (e.g., milk, bread) tracked or monitored by smart refrigerators. In another instance, the attribute data may include utility usage data (e.g., electricity, water). Analysis of the utility usage data may indicate patterns or status of the user, such as, the user being on vacation, the user being ill (e.g., increasing house thermostat set temperature to cope with a cold), the user being an energy conscious consumer, and so on.

Figure 13:
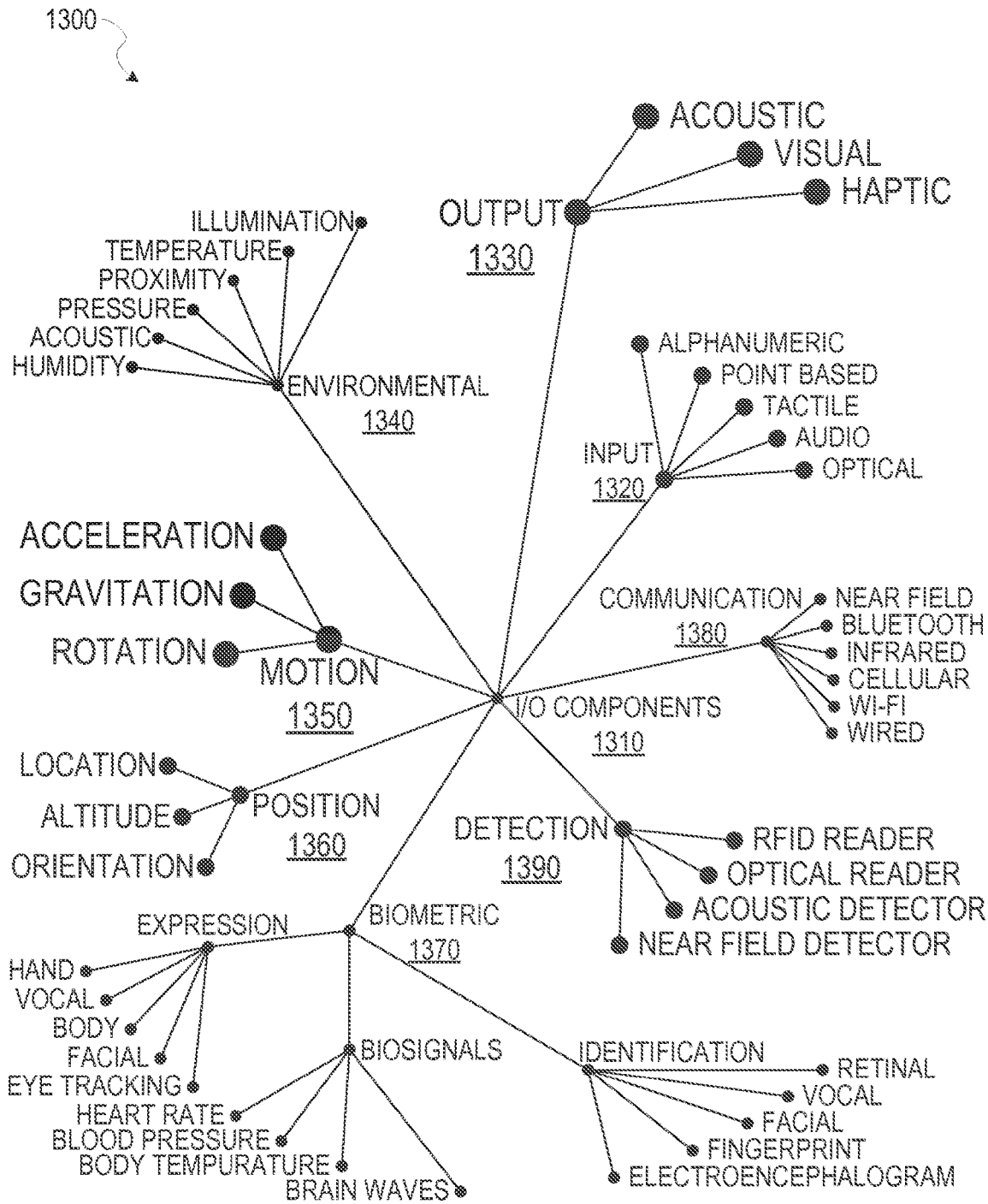
FIG. 13 depicts various components that provide attribute data, according to some example embodiments.

FIG. 13 depicts non-limiting example components 1300 that may provide attribute data according to some example embodiments. In example embodiments, I/O components 1310 may include input components 1320, output components 1330, environmental components 1340, motion components 1350, position components 1360, biometric components 1370, communication components 1380, detection components 1390, and a wide gamut of other sensors, gauges, and measurement components. The I/O components 1310 or a suitable combination of the I/O components 1310 may be included in any suitable device or machine such as those included in the attribute sources 1210 depicted in FIG. 12 to facilitate the functionality described herein. In various example embodiments, the attribute data provided by the I/O components 1310 may be accessible to all or some of the modules described above on a real-time or near real-time basis. The components 1300 are grouped according to functionality merely for simplifying the following discussion and the grouping is in no way limiting.

The input components 1320 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provide location and force of touches or touch gestures, or other tactile input components), audio input components (e.g., a microphone), and the like. The input components 1320 may receive input from the user to facilitate the functionalities described herein. For instance, the user may interact with a user interface using the input components 1320.

The output components 1330 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The output components 1330 may present information to the user. For example, the output components 1330 may present a user interface to the user or present media files to the user.

The environmental components 1340 may include illumination sensors (e.g., photometer), temperature sensors (e.g., one or more thermometers that detect ambient temperature), humidity sensors, pressure sensors (e.g., barometer), acoustic sensors (e.g., one or more microphone that detects background noise), proximity sensors (e.g., an infrared sensor that detects nearby objects), gas sensors (e.g., gas detection sensors to detection concentrations of hazardous gases for safety or to measure pollutants in the atmosphere), and so on. The environmental components 1340 may measure various physical parameters to provide an indication or signal corresponding to the physical environment surrounding the environmental components 1340.

The motion components 1350 may include acceleration sensors (e.g., accelerometer), gravitation sensors, rotation sensors (e.g., gyroscope), and so forth. The motion components 1350 may provide motion data such as velocity, acceleration, or other force measurements along an x, y, and z axes. The motion data may be provided at a regular update rate (e.g., 10 updates per second) that may be configurable.

The position components 1360 may include location sensors (e.g., a Global Position System (GPS) receiver component), altitude sensors (e.g., altimeters or barometers that detect air pressure from which altitude may be derived), orientation sensors (e.g., magnetometers that provide magnetic field strength along the x, y, and z axes), and the like. In an example embodiment, the position components 1360 may provide position data such as latitude, longitude, altitude, and a time stamp. Similar to the motion components 1350, the position components 1360 may provide the motion data at a regular update rate that may be configurable.

The biometric components 1370 may include components to detect expressions, measure biosignals, or identify people, among other functions. For example, the biometric components 1370 may include expression components to detect expressions (also referred to as "kinesics") such as hand gestures (e.g., an optical component to detect a hand gesture or a Doppler component to detect hand motions), vocal expressions (e.g., a microphone to detect changes in voice pitch that may indicate tension), facial expressions (e.g., a camera to detect expressions or micro-expressions of a person such as a smile), body gestures, and eye tracking (e.g., detecting the focal point of a person's eyes or patterns in eye movement). The biometric components 1370 may also include, for example, biosignal components to measure biosignals such as blood pressure, heart rate, body temperature, perspiration, and brain waves (e.g., as determined by a electroencephalogram). In further examples, the biometric components 1370 may include identification components to identify people such as retinal scanners (e.g., a camera component), vocal detectors (e.g., a microphone to receive audio data for voice identification), facial detectors, fingerprint detectors, and electroencephalogram sensors (e.g., to identify a person via unique brain wave patterns).

Communication may be implemented using a wide variety of technologies. The I/O components 1310 may include communication components 1380 operable to communicatively couple machines or devices. For example, the communication components 1380 may include a network interface component or other suitable device to interface with a network (e.g., the network 104). In further examples, the communication components 1380 may include wired communication components, wireless communication components, cellular communication components, Near Field Communication (NFC) components, Bluetooth® components (e.g., Bluetooth® Low Energy), Wi-Fi® components, and other communication components to provide communication via other modalities. In addition, a variety of information may be derived using the communication components 1380 such as location via Internet Protocol (IP) geo-location, location via Wi-Fi® signal triangulation, location via detecting a NFC beacon signal that may indicate a particular location, and so forth.

The I/O components 1310 may include detection components 1390 that may detect a variety of identifiers. For example, the detection components 1390 may include Radio Frequency Identification (RFID) tag reader components, Near Field Communication (NFC) smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), and acoustic detection components (e.g., microphones to identify tagged audio signals).

Figure 14:
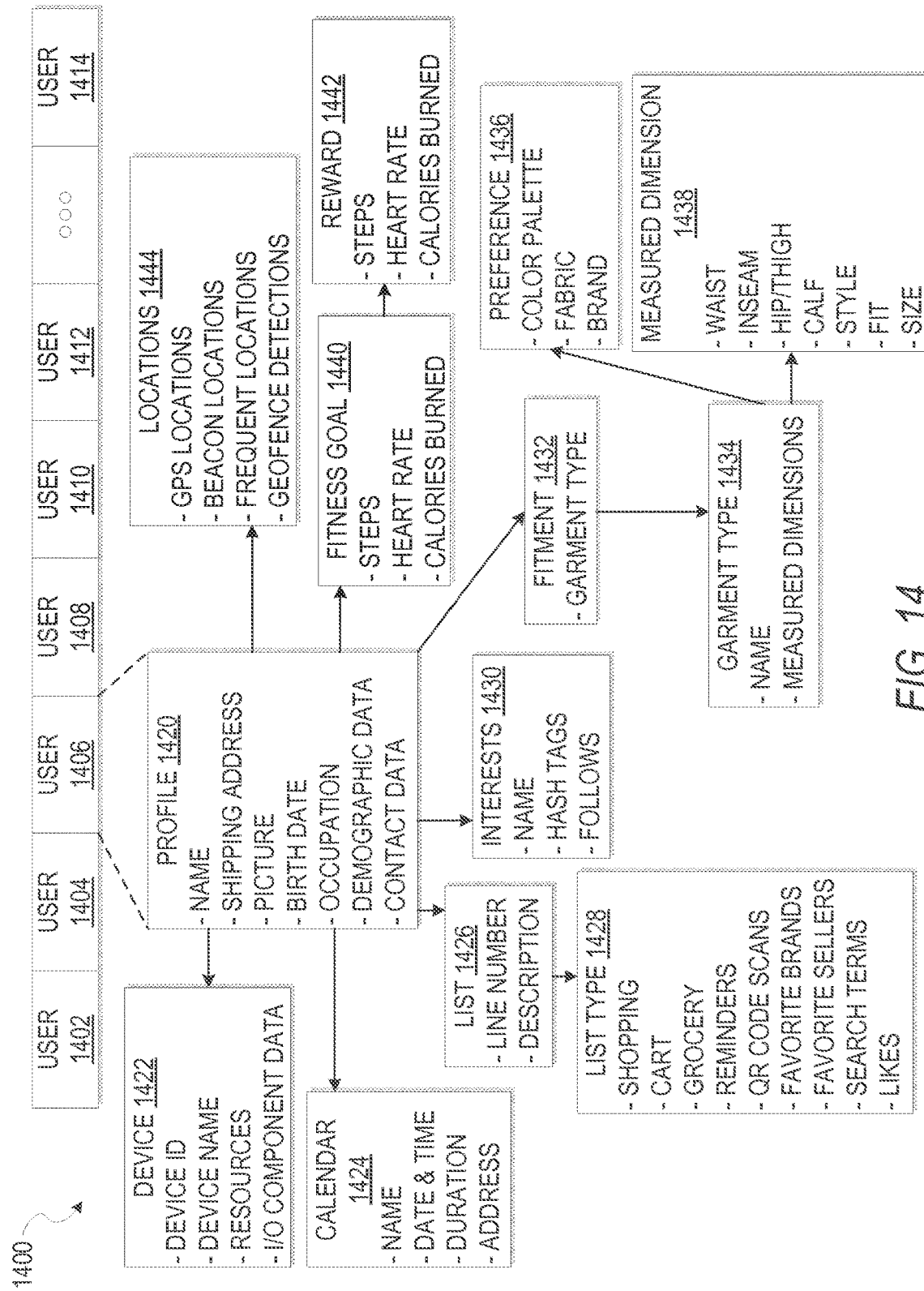
FIG. 14 is a block diagram of an example data structure for example attribute data associated with a user, according to some example embodiments.

FIG. 14 is a block diagram 1400 of an example data structure for the attribute data associated with a particular user according to example embodiments. In example embodiments, the attribute data may be associated with a plurality of users such as user 1402, 1404, 1406, 1408, 1410, 1412, and 1414. In an example embodiment, the attribute data may be accessed for a particular user by using a user identifier. The attribute data may include profile data 1420, device data 1422, calendar data 1424, list data 1426, list type data 1428, interest data 1430, fitment data 1432, garment type data 1434, preference data 1436, measured dimension data 1438, fitness goal data 1440, reward data 1442, location data 1444, and other data not shown. In some example embodiments, the attribute data may be structured such that various portions of the attribute data are associated with other portions of the attribute data via relationships. For instance, the calendar data 1424 may include a calendar event associated with an event name, an event data, and an event location for the calendar event.

FIG. 15 is a block diagram 1500 of an example data structure for data associated with a device according to some example embodiments. In an example embodiment, the device data 1422 of FIG. 14 may include a device identifier, a device name, device resources data (e.g., files stores on the devices such as browser cookies, media files), I/O component data, and so forth. In example embodiments, the device identifier may, for example, comprise an Internet Protocol (IP) address, a Media Access Control (MAC) address, other unique identifies, an International Mobile Station Equipment Identity (IMEI), or a Mobile Equipment Identifier (MEID). In an example embodiment, the I/O component data may include standard device parameters 1502, position data 1504, location data 1506, motion data 1508, environmental data 1510, biometric data 1512, and other data. FIG. 15 merely depicts example attribute data that may correspond to a particular device, and a variety of other data not shown may be included in the device data. The standard device parameters 1502 may include parameters that are standard across multiple devices included in the IoT. In various example embodiments, standardized parameters and protocols may facilitate access and utilization of the attribute data corresponding to such devices. For example, the attribute data available on an unknown device may be accessed and utilized without the need to discover or otherwise determine which parameters are available and which units of measure are associated with the parameters. Many other schemes may be employed to discover or otherwise determine available parameters accessible on a particular device.

Modules, Components, and Logic

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a Field-Programmable Gate Array (FPGA) or an Application Specific Integrated Circuit (ASIC). A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software may accordingly configure a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

Applications

Figure 16:
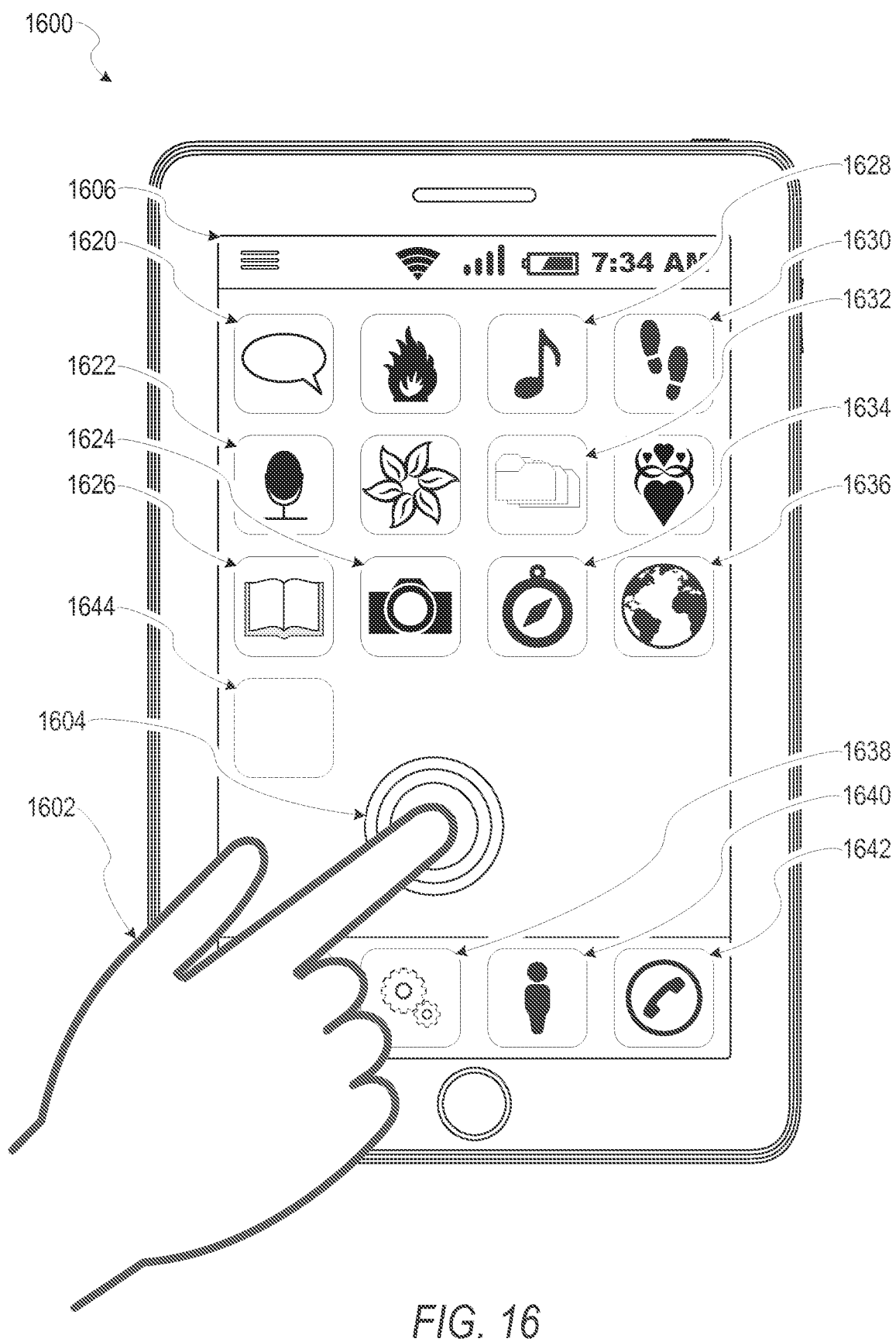
FIG. 16 depicts an example mobile device and mobile operating system interface, according to some example embodiments.

FIG. 16 illustrates an example mobile device 1600 that may be executing a mobile operating system (e.g., iOS™, Android™, Windows® Phone, or other mobile operating systems), according to example embodiments. In one embodiment, the mobile device 1600 may include a touch screen that may receive tactile information from a user 1602. For instance, the user 1602 may physically touch 1604 the mobile device 1600, and in response to the touch 1604, the mobile device 1600 may determine tactile information such as touch location, touch force, gesture motion, and so forth. In various example embodiment, the mobile device 1600 may display home screen 1606 (e.g., Springboard on iOS™) that the user 1602 of the mobile device 1600 may use to launch applications and otherwise manage the mobile device 1600. In various example embodiments, the home screen 1606 may provide status information such as battery life, connectivity, or other hardware status. The home screen 1606 may also include a plurality of icons that may be activated to launch applications, for example, by touching the area occupied by the icon. Similarly, other user interface elements may be activated by touching an area occupied by a particular user interface element. In this manner, the user 1602 may interact with the applications.

Many varieties of applications (also referred to as "apps") may be executing on the mobile device 1600. The applications may include native applications (e.g., applications programmed in Objective-C running on iOS™ or applications programmed in Java running on Android™), mobile web applications (e.g., HTML5), or hybrid applications (e.g., a native shell application that launches an HTML5 session). In a specific example, the mobile device 1600 may include a messaging app 1620, audio recording app 1622, a camera app 1624, a book reader app 1626, a media app 1628, a fitness app 1630, a file management app 1632, a location app 1634, a browser app 1636, a settings app 1638, a contacts app 1640, a telephone call app 1642, other apps (e.g., gaming apps, social networking apps, biometric monitoring apps), a third party app 1644, and so forth.

Software Architecture

Figure 17:
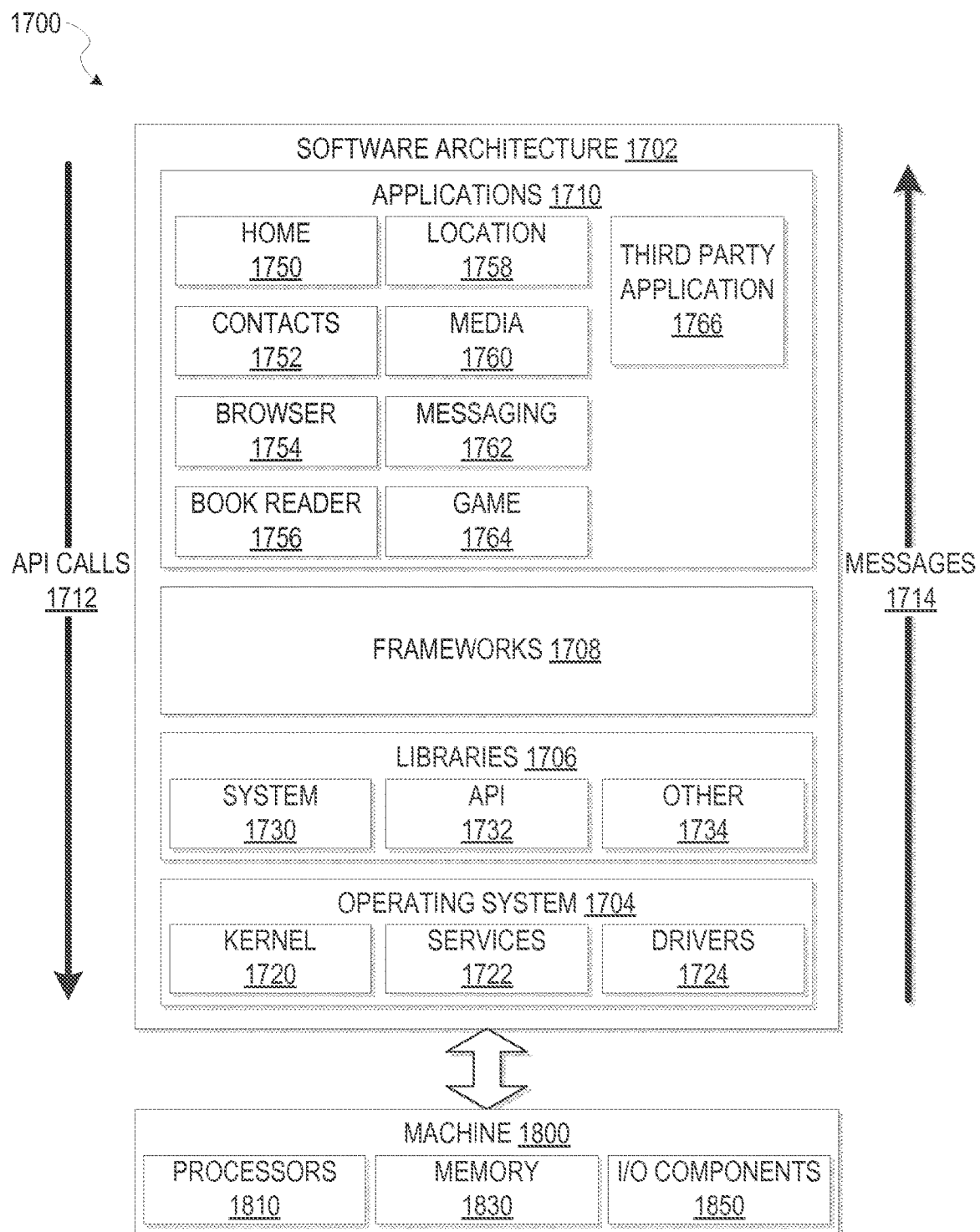
FIG. 17 is a block diagram illustrating an example of a software architecture that may be installed on a machine, according to some example embodiments.

FIG. 17 is a block diagram 1700 illustrating an architecture of software 1702, which may be installed on any one or more of devices described above. FIG. 17 is merely a non-limiting example of a software architecture and it will be appreciated that many other architectures may be implemented to facilitate the functionality described herein. The software 1702 may be executing on hardware such as machine 1800 of FIG. 18 that includes processors 1810, memory 1830, and I/O components 1850. In the example architecture of FIG. 17, the software 1702 may be conceptualized as a stack of layers where each layer may provide particular functionality. For example, the software 1702 may include layers such as an operating system 1704, libraries 1706, frameworks 1708, and applications 1710. Operationally, the applications 1710 may invoke application programming interface (API) calls 1712 through the software stack and receive messages 1714 in response to the API calls 1712.

The operating system 1704 may manage hardware resources and provide common services. The operating system 1704 may include, for example, a kernel 1720, services 1722, and drivers 1724. The kernel 1720 may act as an abstraction layer between the hardware and the other software layers. For example, the kernel 1720 may be responsible for memory management, processor management (e.g., scheduling), component management, networking, security settings, and so on. The services 1722 may provide other common services for the other software layers. The drivers 1724 may be responsible for controlling or interfacing with the underlying hardware. For instance, the drivers 1724 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth.

The libraries 1706 may provide a low-level common infrastructure that may be utilized by the applications 1710. The libraries 1706 may include system 1730 libraries (e.g., C standard library) that may provide functions such as memory allocation functions, string manipulation functions, mathematic functions, and the like. In addition, the libraries 1706 may include API libraries 1732 such as media libraries (e.g., libraries to support presentation and manipulation of various media formats such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1706 may also include a wide variety of other libraries 1734 to provide many other APIs to the applications 1710.

The frameworks 1708 may provide a high-level common infrastructure that may be utilized by the applications 1710. For example, the frameworks 1708 may provide various graphic user interface (GUI) functions, high-level resource management, high-level location services, and so forth. The frameworks 1708 may provide a broad spectrum of other APIs that may be utilized by the applications 1710, some of which may be specific to a particular operating system or platform.

The applications 1710 include a home application 1750, a contacts application 1752, a browser application 1754, a book reader application 1756, a location application 1758, a media application 1760, a messaging application 1762, a game application 1764, and a broad assortment of other applications such as third party application 1766. In a specific example, the third party application 1766 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third party application 1766 may invoke the API calls 1712 provided by the mobile operating system 1704 to facilitate functionality described herein.

Example Machine Architecture and Machine-Readable Medium

Figure 18:
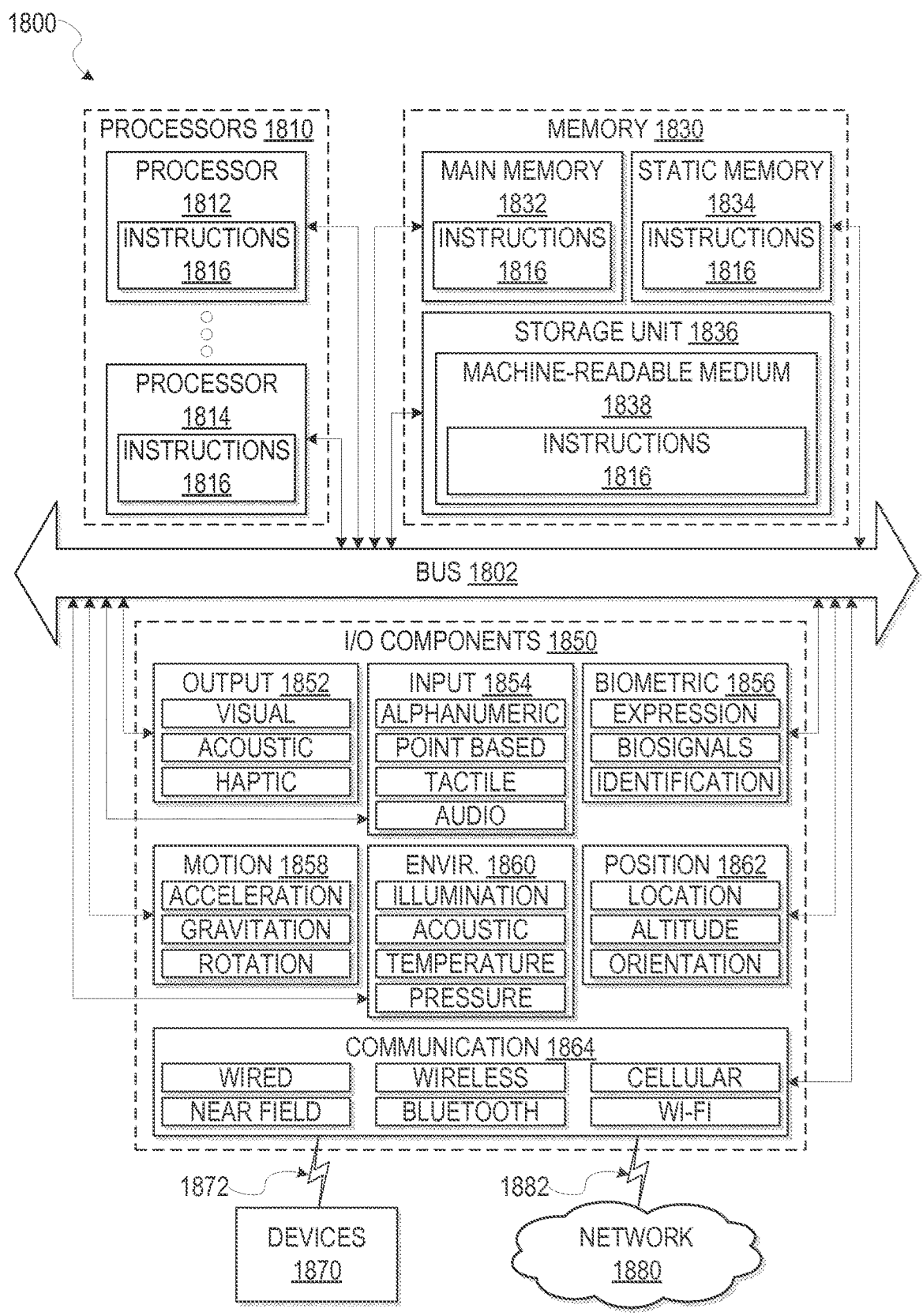
FIG. 18 illustrates a diagrammatic representation of a machine in the form of a computer system within which a set of instructions may be executed for causing the machine to perform any one or more of the methodologies discussed herein, according to an example embodiment.

FIG. 18 is a block diagram illustrating components of a machine 1800, according to some example embodiments, able to read instructions from a machine-readable medium (e.g., a machine-readable storage medium) and perform any one or more of the methodologies discussed herein. Specifically, FIG. 18 shows a diagrammatic representation of the machine 1800 in the example form of a computer system, within which instructions 1816 (e.g., software, a program, an application, an applet, an app, or other executable code) for causing the machine 1800 to perform any one or more of the methodologies discussed herein may be executed. In alternative embodiments, the machine 1800 operates as a standalone device or may be coupled (e.g., networked) to other machines. In a networked deployment, the machine 1800 may operate in the capacity of a server machine or a client machine in a server-client network environment, or as a peer machine in a peer-to-peer (or distributed) network environment. The machine 1800 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1816, sequentially or otherwise, that specify actions to be taken by machine 1800. Further, while only a single machine 1800 is illustrated, the term "machine" shall also be taken to include a collection of machines 1800 that individually or jointly execute the instructions 1816 to perform any one or more of the methodologies discussed herein.

The machine 1800 may include processors 1810, memory 1830, and I/O components 1850, which may be configured to communicate with each other via a bus 1802. In an example embodiment, the processors 1810 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 1812 and processor 1814 that may execute instructions 1816. The term "processor" is intended to include multi-core processor that may comprise two or more independent processors (also referred to as "cores") that may execute instructions contemporaneously. Although FIG. 18 shows multiple processors, the machine 1800 may include a single processor with a single core, a single processor with multiple cores (e.g., a multi-core process), multiple processors with a single core, multiple processors with multiples cores, or any combination thereof.

The memory 1830 may include a main memory 1832, a static memory 1834, and a storage unit 1836 accessible to the processors 1810 via the bus 1802. The storage unit 1836 may include a machine-readable medium 1838 on which is stored the instructions 1816 embodying any one or more of the methodologies or functions described herein. The instructions 1816 may also reside, completely or at least partially, within the main memory 1832, within the static memory 1834, within at least one of the processors 1810 (e.g., within the processor's cache memory), or any suitable combination thereof, during execution thereof by the machine 1800. Accordingly, the main memory 1832, static memory 1834, and the processors 1810 may be considered as machine-readable media 1838.

As used herein, the term "memory" refers to a machine-readable medium 1838 able to store data temporarily or permanently and may be taken to include, but not be limited to, random-access memory (RAM), read-only memory (ROM), buffer memory, flash memory, and cache memory. While the machine-readable medium 1838 is shown in an example embodiment to be a single medium, the term "machine-readable medium" should be taken to include a single medium or multiple media (e.g., a centralized or distributed database, or associated caches and servers) able to store instructions 1816. The term "machine-readable medium" shall also be taken to include any medium, or combination of multiple media, that is capable of storing instructions (e.g., instructions 1816) for execution by a machine (e.g., machine 1800), such that the instructions, when executed by one or more processors of the machine 1800 (e.g., processors 1810), cause the machine 1800 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory (e.g., flash memory), an optical medium, a magnetic medium, other non-volatile memory (e.g., Erasable Programmable Read-Only Memory (EPROM)), or any suitable combination thereof. The term "machine-readable medium" specifically excludes non-statutory signals per se.

The I/O components 1850 may include a wide variety of components to receive input, provide output, produce output, transmit information, exchange information, capture measurements, and so on. It will be appreciated that the I/O components 1850 may include many other components that are not shown in FIG. 18. The I/O components 1850 are grouped according to functionality merely for simplifying the following discussion and the grouping is in no way limiting. In various example embodiments, the I/O components 1850 may include output components 1852 and input components 1854. The output components 1852 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The input components 1854 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and force of touches or touch gestures, or other tactile input components), audio input components (e.g., a microphone), and the like.

In further example embodiments, the I/O components 1850 may include biometric components 1856, motion components 1858, environmental components 1860, or position components 1862 among a wide array of other components. For example, the biometric components 1856 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1858 may include acceleration sensor components (e.g., accelerometer), gravitation sensor components, rotation sensor components (e.g., gyroscope), and so forth. The environmental components 1860 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1862 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1850 may include communication components 1864 operable to couple the machine 1800 to a network 1880 or devices 1870 via coupling 1882 and coupling 1872 respectively. For example, the communication components 1864 may include a network interface component or other suitable device to interface with the network 1880. In further examples, communication components 1864 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1870 may be another machine or any of a wide variety of peripheral devices (e.g., a peripheral device coupled via a Universal Serial Bus (USB)).

Moreover, the communication components 1864 may detect identifiers or include components operable to detect identifiers. For example, the communication components 1864 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1864, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 1880 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1880 or a portion of the network 1880 may include a wireless or cellular network and the coupling 1882 may be a Code Division Multiple Access (CDMA) connection, a Global System for Mobile communications (GSM) connection, or other type of cellular or wireless coupling. In this example, the coupling 1882 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 1816 may be transmitted or received over the network 1880 using a transmission medium via a network interface device (e.g., a network interface component included in the communication components 1864) and utilizing any one of a number of well-known transfer protocols (e.g., hypertext transfer protocol (HTTP)). Similarly, the instructions 1816 may be transmitted or received using a transmission medium via the coupling 1872 (e.g., a peer-to-peer coupling) to devices 1870. The term "transmission medium" shall be taken to include any intangible medium that is capable of storing, encoding, or carrying instructions 1816 for execution by the machine 1800, and includes digital or analog communications signals or other intangible medium to facilitate communication of such software.

Furthermore, the machine-readable medium 1838 is non-transitory (in other words, not having any transitory signals) in that it does not embody a propagating signal. However, labeling the machine-readable medium 1838 as "non-transitory" should not be construed to mean that the medium is incapable of movement, the medium should be considered as being transportable from one physical location to another. Additionally, since the machine-readable medium 1838 is tangible, the medium may be considered to be a machine-readable device.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. A system comprising:
   at least one hardware processor; and
   a memory storing instructions that, when executed by the at least one hardware processor cause the system to perform operations comprising:
   generating an avatar representation of a user;
   receiving user input comprising a user-specified change to the avatar representation;
   changing the avatar representation based on the user-specified change to the avatar representation;
   receiving, from a first client device, user data associated with a user of the publication system;
   determining a facial expression of the user based on the user data;
   determining a graphical representation of the facial expression of the user;
   generating an updated avatar representative of a current status of the user by applying the graphical representation of the facial expression of the user to the avatar representation of the user; and
   causing one or more second client devices to display the updated avatar in association with a communication of the user.

2. The system of claim 1, wherein the operations further comprise:
   generating the avatar representation of the user based on the user data, the user data including attribute data descriptive of the user, the attribute data comprises demographic data and social media content of the user.

3. The system of claim 2, wherein:
   the generating of the avatar representation of the user comprises inferring visually exemplifiable user characteristics corresponding to the user based on an analysis of the attribute data, the user characteristics comprising a physical trait and a personality trait; and
   the generating of the avatar representation of the user is based at least in part on the inferred physical trait and the inferred personality trait.

4. The system of claim 2, wherein the operations further comprise receiving, the attribute data from a plurality of attribute sources comprising a plurality of electronic devices.

5. The system of claim 1, wherein the operations further comprise:
   inferring subsequent user characteristics based, at least in part, on the user input; and
   wherein the changing the avatar representation is based, at least in part, on the subsequent user characteristics.

6. The system of claim 1, wherein the user input comprises a user interaction with the updated avatar.

7. The system of claim 1, wherein the user data includes data from one or more biometric components of the first client device, the one or more biometric components being configured to detect one or more kinesics associated with the user.

8. The system of claim 1, wherein the user data includes real-time sensor data produced by one or more sensors of the first client device.

9. The system of claim 1, wherein the operations further comprise:
   determining satisfaction of a reward criteria associated with the user data; and
   providing a reward to the user based on the determined satisfaction of the reward criteria, wherein the reward comprises a visualization feature.

10. The system of claim 1, wherein the reward criteria includes a criterion based on at least one of a completeness metric or a quality metric, the completeness metric indicating a quantity of a specified type of data included in the user data, the quality metric indicating a recentness of the user data.

11. A method comprising:
    generating an avatar representation of a user;
    receiving user input comprising a user-specified change to the avatar representation;
    changing the avatar representation based on the user-specified change to the avatar representation;
    receiving, from a first client device, user data associated with a user of the publication system;
    determining a facial expression of the user based on the user data;
    determining a graphical representation of the facial expression of the user;
    generating an updated avatar representative of a current status of the user by applying the graphical representation of the facial expression of the user to the avatar representation of the user; and
    causing one or more second client devices to display the updated avatar in association with a communication of the user.

12. The method of claim 11, further comprising generating the avatar representation of the user based on the user data, the user data including attribute data descriptive of the user, the attribute data comprises demographic data and social media content of the user.

13. The method of claim 12, wherein:
    the generating of the avatar representation of the user comprises inferring visually exemplifiable user characteristics corresponding to the user based on an analysis of the attribute data, the user characteristics comprising a physical trait and a personality trait; and
    the generating of the avatar representation of the user is based at least in part on the inferred physical trait and the inferred personality trait.

14. The method of claim 12, wherein the operations further comprise receiving, the attribute data from a plurality of attribute sources comprising a plurality of electronic devices.

15. The method of claim 11, further comprising:
    inferring subsequent user characteristics based, at least in part, on the user input; and
    wherein the changing of the avatar representation is based, at least in part, on the subsequent user characteristics.

16. The method of claim 11, wherein the user input comprises a user interaction with the updated avatar.

17. The method of claim 11, wherein the user data includes data from one or more biometric components of the first client device, the one or more biometric components being configured to detect one or more kinesics associated with the user.

18. The method of claim 11, wherein the user data includes real-time sensor data produced by one or more sensors of the first client device.

19. The method of claim 11, wherein the operations further comprise:
 determining satisfaction of a reward criteria associated with the user data; and
 providing a reward to the user based on the determined satisfaction of the reward criteria, wherein the reward comprises a visualization feature.

20. A non-transitory machine-readable medium storing instructions that, when executed by at least one processor of a machine, cause the machine to perform operations comprising:
 generating an avatar representation of a user;
 receiving user input comprising a user-specified change to the avatar representation;
 changing the avatar representation based on the user-specified change to the avatar representation;
 receiving, from a first client device, user data associated with a user of the publication system;
 determining a facial expression of the user based on the user data;
 determining a graphical representation of the facial expression of the user;
 generating an updated avatar representative of a current status of the user by applying the graphical representation of the facial expression of the user to the avatar representation of the user; and
 causing one or more second client devices to display the updated avatar in association with a communication of the user.

* * * * *